: patent document

United States Patent [19]
Rhett et al.

[11] Patent Number: 5,839,091
[45] Date of Patent: Nov. 17, 1998

[54] METHOD AND APPARATUS FOR AUTOMATIC TISSUE STAINING

[75] Inventors: Norman K. Rhett, San Ramon; Ken K. Tseung, Fremont; Mark V. Corl, Fremont; Wai Bun Wong, Fremont; Ngoc Van Le, Milpitas, all of Calif.

[73] Assignee: Lab Vision Corporation, Fremont, Calif.

[21] Appl. No.: 726,702

[22] Filed: Oct. 7, 1996

[51] Int. Cl.$^6$ .................................................. G01N 33/53
[52] U.S. Cl. ............................... 702/19; 422/63; 422/67; 422/49
[58] Field of Search .............................. 364/500; 422/63, 422/99, 67; 252/408

[56] References Cited

U.S. PATENT DOCUMENTS

| | | | |
|---|---|---|---|
| 4,141,312 | 2/1979 | Louder et al. | 118/7 |
| 5,073,504 | 12/1991 | Bogen | 436/174 |
| 5,116,759 | 5/1992 | Klainer et al. | 435/288 |
| 5,355,439 | 10/1994 | Bernstein et al. | 395/82 |
| 5,439,649 | 8/1995 | Tseung et al. | 422/99 |
| 5,573,727 | 11/1996 | Keefe | 422/63 |
| 5,654,199 | 8/1997 | Copeland et al. | 436/46 |

FOREIGN PATENT DOCUMENTS

| | | |
|---|---|---|
| WO9113335 | 9/1991 | WIPO . |
| WO9201919 | 2/1992 | WIPO . |

OTHER PUBLICATIONS

Leica, "Automated Tissue Staining for Immunohistochemistry", Feb. 6, 1992, 8 pages.
BioGenex, "Optimax™ Automated Cell Staining System", 4 pages.
Biotek™ Solutions, "Automated Immunostaining Systems", 1993, 12 pages.
Sakura World Class Technology™, "RSG–61 Hematology Slide Stainer", 1995, 2 pages.
Beckman, "Biomek® 2000 Automated Workstation", 2 page form.
Ventana, "Ventana in Situ Hybridization System", Rev–Mar. 31, 1994, 1 page.
Shandon Cadenza®, "Automated Immunostainer", 1989, pp. 1–8.
Hamilton, "Microlab® SPE", 1pg (front and back).
Matrix Technologies Corporation, "Automated Sample Handling", Sep. 1993, 4 pages.
Packard, "Multiprobe® Robotic Liquid Handling", 8 page newsletter and pp. 8–9.
Rosys, "Introduce a new philosophy into your laboratory!", 1 page.
Tecan US, Inc., "Progressing as One in Laboratory Automation", 9 page brochure.

*Primary Examiner*—Emanuel Todd Voeltz
*Assistant Examiner*—Matthew W. Smithers
*Attorney, Agent, or Firm*—Blakely, Sokoloff, Taylor & Zafman LLP

[57] ABSTRACT

To simplify the process of preparing microscope slides, an advanced automatic staining apparatus is disclosed. The disclosed automatic staining apparatus comprises an electromechanical automatic staining device that is coupled to a personal computer system using an interface card. An autostainer control program runs on the personal computer system. The autostainer control program allows a user to simply program the automatic staining apparatus using simple commands entered in the graphical user interface. The autostainer control program includes several features that simplify the programming such as safeguards that ensure compatible reagents are being used; automatic buffer solution requirement calculator; and the ability to determine optimal staining procedure. The electromechanical automatic staining device includes features such as dual waste bins for hazardous and nonhazardous waste storage, an automatic dispenser cleansing system; and unique slide clip that minimizes capillary effect.

29 Claims, 34 Drawing Sheets

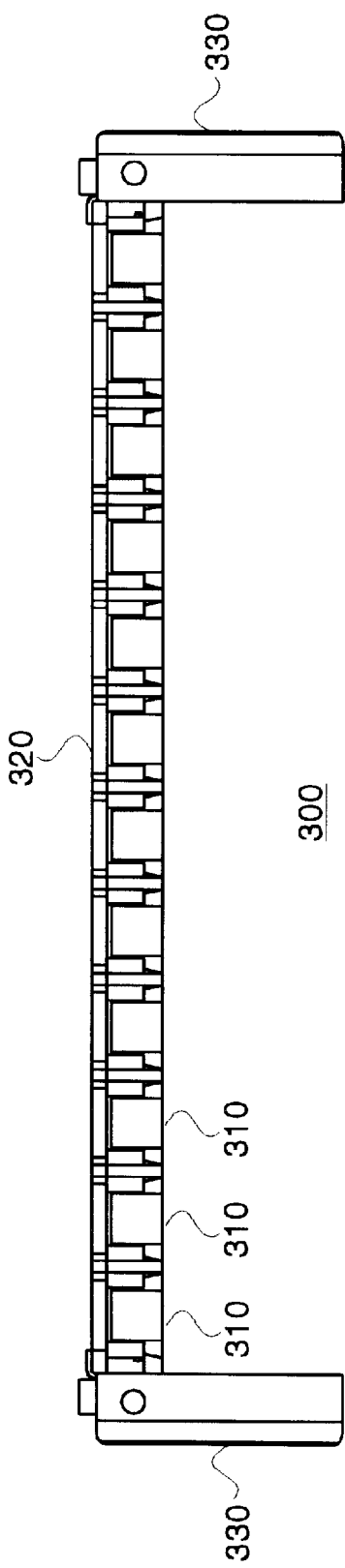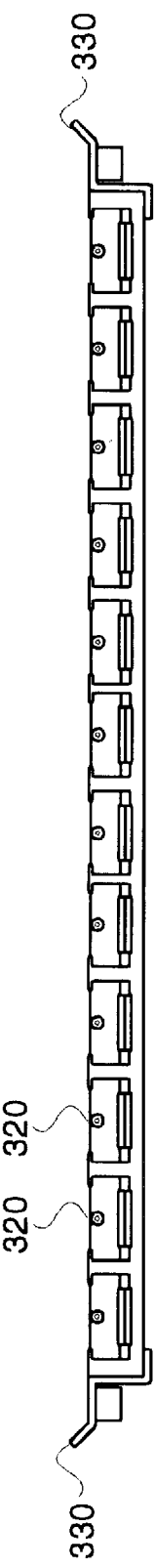
Figure 3a
Figure 3b

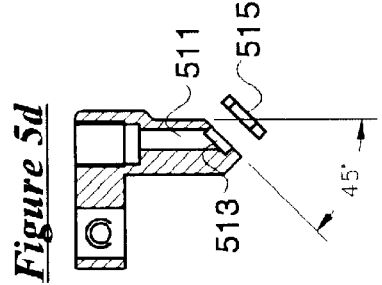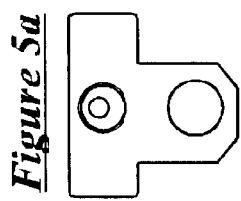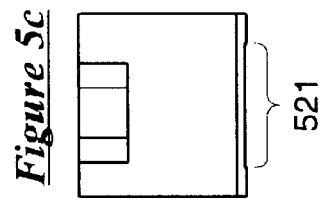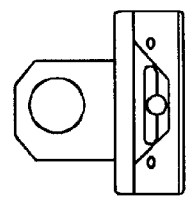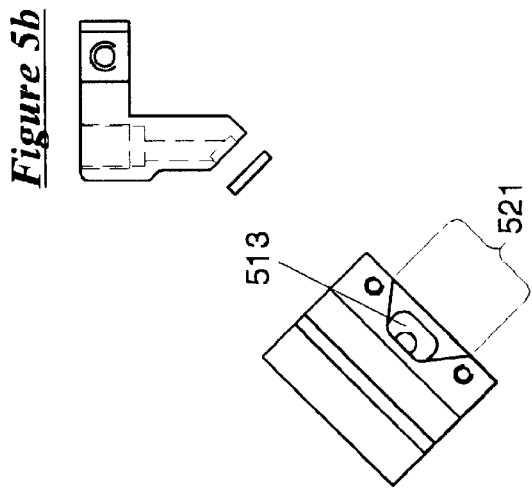

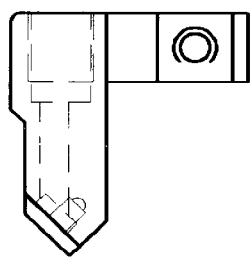
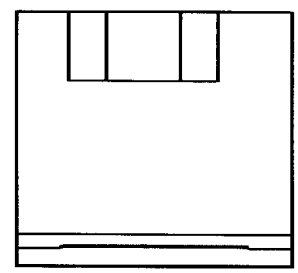
Figure 5g
Figure 5h

| Program Staining Run | | | | | | | | | | | ☒ |
|---|---|---|---|---|---|---|---|---|---|---|---|
| File   Edit lists   Copy   Auto | | | | | | | | | | | |
| Slide # | Patient Name Case # | Doctor Name | Rinse | End Enz. Block 200 µl | Rinse | Pretreatment Antibody 200 µl | Rinse | Primary Antibody 200 µl | Rinse | Secondary Reagent 200 µl | |
| 1 | | | | | | | | | | | |
| 2 | | | | | | | | | | | |
| 3 | | | | | | | | | | | |
| 4 | | | | | | | | | | | |
| 5 | | | | | | | | | | | |
| 6 | | | | | | | | | | | |
| 7 | | | | | | | | | | | |
| Program: | | | | | | | | | | | |
| Patient Info | Protocol Template | | | | Run | | Print | | Exit | Help | |

| Slide # | Patient Name Case # | Doctor Name | R i n s e | Pretreatment 200 μl | R i n s e | Primary Antibody 200 μl | R i n s e | Secondary Reagent 200 μl | R i n s e | Tertiary Reagea 200 μl |
|---|---|---|---|---|---|---|---|---|---|---|
| 41 | a, a | Dr. Mark | | | | Calci 10' | | BixMxR 10' | | SA-HRP 10' |
| 42 | a, a | Dr. Mark | | | | NCCalc 10' | | BixMxR 10' | | SA-HRP 10' |
| 43 | a, a | | | | | | | | | SA-HRP 10' |
| 44 | a, a | | | | | | | | | SA-HRP 10' |
| 45 | a, a | | | | | | | | | SA-HRP 10' |
| 46 | a, a | Dr. Mark | | | | VimV9 10' | | BixMxR 10' | | SA-HRP 10' |
| 47 | a, a | Dr. Mark | | | | NCV9 10' | | BixMxR 10' | | SA-HRP 10' |

Program Staining Run

File  Edit lists  Copy  Auto

Which Report?

[ Main Grid ]  [ I.H.C. ]  [ Cancel ]

Program: canada-1

[ Patient Info ] [ Protocol Template ] [ Run ] [ Print ] [ Exit ] [ Help ]

*Figure 9b*

Patient Information

Enter last name or last, first mi

- Patient Name | John, Smith ▼ ~1011
- Patient Case # | 12345 ▼ ~1081
- # Slides/case | 48
- Doctor | Dr. Mark Corl ▼

1010 — [Finish Entry]  
1020 — [Delete]  
1030 — [Cancel]  
1040 — [Help]

You have now entered: 1 patient(s) 1 case(s) 48 slides

*Figure 10*

| Program Staining Run | | | | | | | | | | | |
|---|---|---|---|---|---|---|---|---|---|---|---|
| File  Edit lists  Copy  Auto | | | | | | | | | | | |
| Slide # | Patient Name Case # | Doctor Name | Rinse | End,Enz. Block 300 μl | Rinse | Pretreatment 200 μl | Rinse | Primary Antibody 200 μl | Rinse | Secondary Reagent 200 μl | Rinse |
| 1 | John Smith 12345 | Dr. Mark | 💧 | H202/N 5' | | | | | | | |
| 2 | John Smith 12345 | Dr. Mark | 💧 | | | | | | | | |
| 3 | John Smith 12345 | Dr. N | | | | | | | | | |
| 4 | John Smith 12345 | Dr. N | | | | | | | | | |
| 5 | John Smith 12345 | Dr. N | | | | | | | | | |
| 6 | John Smith 12345 | Dr. N | | | | | | | | | |
| 7 | John Smith 12345 | Dr. Mark | 💧 | | | | | | | | |
| Program: canada-1 | | | | | | | | | | | |
| Patient Info | Protocol Template | | | Run | | Print | | Exit | | Help | |

End, Enz. Block

Assign to following unprogrammed slides
1420    1430

Yes    No

*Figure 14*

| Program Staining Run | | | | | | | | | | | |
|---|---|---|---|---|---|---|---|---|---|---|---|
| File Edit lists Copy Auto | | | | | | | | | | | |
| Slide # | Patient Name Case # | Doctor Name | nd,Enz. lock 00μl | R i n s e | Pretreatment 200 μl | R i n s e | Primary Antibody 200 μl | R i n s e | Detection Kit 200 μl | R i n s e | Aux 200 |
| 1 | John Smith 12345 | Dr. Mark | 202/N 5' | ◊ | | | SMAct 10' | ◊ | | | Cou 5' |
| 2 | John Smith 12345 | Dr. Mark | 202/N 5' | ◊ | Prot24 6' | ◊ | AACT 10' | ◊ | | | Cou 5' |
| 3 | John Smith 12345 | Dr. Mark | 202/N 5' | ◊ | Prot24 6' | ◊ | AAT 10' | ◊ | | | Cou 5' |
| 4 | John Smith 12345 | Dr. Mark | 202/N 5' | ◊ | | | ACTH 10' | ◊ | | | Cou 5' |
| 5 | [none] Envision-HRP-AEC | | 202/N 5' | ◊ | | | bcl-2 30' | ◊ | | | Cou 5' |
| 6 | Envision-HRP-AEC-long Envision-HRP-DAB | | 202/N 5' | ◊ | | | Calci 10' | ◊ | | | Cou 5' |
| 7 | Envision-HRP-DAB-long LSAB2-AP-Fast Red | | 202/N 5' | ◊ | | | CD20 10' | ◊ | | | Cou 5' |
| Progr Pa | LSAB2-AP-New Fuchsin LSAB2-HRP-AEC LSAB2-HRP-DAB | | | | col Template | | Run | | Print Exit | | Help |

| Program Staining Run | | | | | | | | | | |
|---|---|---|---|---|---|---|---|---|---|---|
| File Edit lists Copy Auto | | | | | | | | | | |
| Slide # | Patient Name Case # | Doctor Name | Rinse | Primary Antibody 200 µl | Rinse | Secondary Reagent 200 µl | Rinse | Tertiary Reagent 200 µl | Rinse | Switch | Substrate 200 µl |
| 41 | John Smith 12345 | Dr. Mark | | PSA-m 10' | | BixMxR 10' | | SA-HRP 10' | | | DAB 3' |
| 42 | John Smith 12345 | | | S-100 | | BixMxR | | SA-HRP | | | DAB 3' |
| 43 | John Smith 12345 | | | | | | | -HRP | | | DAB 3' |
| 44 | John Smith 12345 | | | | | | | -HRP | | | DAB 3' |
| 45 | John Smith 12345 | | | | | | | -HRP | | | DAB 3' |
| 46 | John Smith 12345 | | | | | | | -HRP | | | DAB 3' |
| 47 | John Smith 12345 | Dr. Mark | | Kappam 10' | | BixMxR 10' | | SA-HRP 10' | | | DAB 3' |

Incompatible Reagents

AEC
Is incompatible with
Strepatavidin-AP.

Continue?

Yes  No

Program: canada-1

Patient Info | Protocol Template | Run | Print | Exit | Help

*Figure 16*

| Program Staining Run | | | | | | | | | | |
|---|---|---|---|---|---|---|---|---|---|---|
| File  Edit lists  Copy  Auto | | | | | | | | | | |
| Slide # | Patient Name Case # | Doctor Name | R i n s e | Primary Antibody 200 μl | R i n s e | Secondary Reagent 200 μl | R i n s e | Tertiary Reagent 200 μl | R i n s e | S w i c h | Substrate 200 μl |
| 41 | John Smith 12345 | Dr. Mark | | PSA-m 10' | | BixMxR 10' | | SA-HRP 10' | | | DAB 3' |
| 42 | John Smith 12345 | Dr. Mark | | S-100 10' | | BixMxR 10' | | SA-HRP 10' | | | DAB 3' |
| 43 | John Smith 12345 | Dr. Mark | | OPD4 | | BixMxR | | SA-HRP | | | DAB 3' |
| 44 | John Smith 12345 | Dr. | | Run program now — Save program on disk  Yes  No  Cancel | | | | RP | | | DAB 3' |
| 45 | John Smith 12345 | Dr. | | | | | | RP | | | DAB 3' |
| 46 | John Smith 12345 | Dr. | | 10' | | 10' | | RP 10' | | | DAB 3' |
| 47 | John Smith 12345 | Dr. Mark | | Kappam 10' | | BixMxR 10' | | SA-HRP 10' | | | DAB 3' |

Program: canada-1

| Patient Info | Protocol Template | Run | Print | Exit | Help |

Load Reagents

| | | | | | | | |
|---|---|---|---|---|---|---|---|
| A1 H2O2/N 8.2ml | A2 Prot24 1.0ml | A3 TSH 0.4ml | A4 Counte 12.7ml | A5 CD20 0.6ml | A6 CD45RO 0.6ml | A7 Kappam 1.4ml | A8 Lamb-p 0.6ml |
| B1 H2o2 4.7ml | B2 BixMxR 12.7ml | B3 AEC 12.1ml | B4 Somato 0.4ml | B5 NF 7.0ml | B6 HBcAg 1.2ml | B7 SMAct 2.3ml | B8 S-100 0.8ml |
| C1 Pronas 3.4ml | C2 Vim3B4 0.4ml | C3 AEC 4.3ml | C4 CMVc 0.6ml | C5 AAT 1.0ml | C6 HHF35 0.6ml | C7 CMV 0.4ml | C8 NSE-p 0.4ml |
| D1 0.1Pro 0.4ml | D2 SA-HRP 12.7ml | D3 DAB 9.2ml | D4 HSV1 0.6ml | D5 HSV2 0.4ml | D6 IgG 0.4ml | D7 p21 0.8ml | D8 p53 0.4ml |

Reagent List — 2410
Prime Pump — 2420
Slide Map — 2430
Second Rack — 2440
OK — 2450
Cancel — 2460
Print — 2470

*Figure 24*

METHOD AND APPARATUS FOR AUTOMATIC TISSUE STAINING

FIELD OF THE INVENTION

The present invention relates to the field of medical lab equipment. In particular the present invention discloses a fully automated system for staining tissue specimens and cell preparations.

BACKGROUND OF THE INVENTION

It is often difficult to examine of unstained cell and tissue preparations with a microscope due to a lack of contrast between individual cells and the background matrix or between individual parts of cells. To improve the contrast, researchers have applied stains to cell and tissue specimens to be examined. The stains are absorbed differently by the various structures in cells such that the contrast between the different cell structures is improved.

Staining tissue specimens is a nontrivial time consuming process. Often a number of different staining and rinsing stages are required. Each stage requires a specific amount of reagent or buffer and takes a specific amount of time. Thus, trained technicians are often employed to perform such operations. Furthermore, hospitals and laboratories must stain large numbers of tissue specimens. Thus, it is desirable to automate the tissue specimen staining process. By automating the process, expensive human labor is eliminated and the probability of an error occurring during the staining process is reduced. Accordingly, a few manufacturers have introduced equipment for the automated staining of tissue specimens on microscope slides.

Existing automatic staining devices are not very simple to use. Arcane programming commands and complicated procedures require extensive user training before such devices can be operated effectively. It would therefore be desirable to simplify the operation of an automatic staining device.

SUMMARY OF THE INVENTION

It is therefore the objective of the present invention to simplify the process of programming an automatic staining apparatus. The present invention comprises an automatic staining apparatus coupled to a personal computer system running an operating system with a graphical user interface. The personal computer system includes an interface card that is used to control the automatic staining apparatus. An autostainer control program runs on the personal computer system. The autostainer control program allows a user to simply program the automatic staining apparatus using simple commands entered in the graphical user interface.

Other objects feature and advantages of present invention will be apparent from the company drawings and from the detailed description that follows below.

BRIEF DESCRIPTION OF THE DRAWINGS

The objects, features and advantages of the present invention will be apparent to one skilled in the art, in view of the following detailed description in which:

FIG. 3a illustrates a top view of a slide rack for the autostainer.

FIG. 3b illustrates a front view of a slide rack for the autostainer.

FIG. 5a illustrates top view of the air nozzle.

FIG. 5b illustrates left side external view of the air nozzle and the nozzle lip.

FIG. 5c illustrates front view of the air nozzle.

FIG. 5d illustrates right side cutaway view of the air nozzle and the nozzle lip.

FIG. 5e illustrates a view of the air nozzle tip.

FIG. 5f illustrates a bottom view of the air nozzle.

FIG. 5g illustrates left side external view of the air nozzle with the nozzle lip in place.

FIG. 5h illustrates front view of the air nozzle.

FIG. 9a illustrates the Program Staining Run Screen of the autostainer control program.

FIG. 9b illustrates the Program Staining Run Screen with a Print Report dialogue box displayed.

FIG. 10 illustrates the Patient Information Screen of the autostainer control program.

FIG. 13 illustrates the Edit Individual Slide Reagent Screen of FIG. 12 with the fields filled in.

FIG. 14 illustrates the Program Staining Run Screen of the autostainer control program with an autoprogramming pop-up window displayed.

FIG. 15 illustrates the Program Staining Run Screen of the autostainer control program with a Detection Kit list for a selected Detection Kit step.

FIG. 16 illustrates the Program Staining Run Screen of the autostainer control program with an incompatible reagent warning dialogue box.

FIG. 18 illustrates the Program Staining Run Screen with a save current program dialogue box.

FIG. 19 illustrates the Slide Layout Map Screen of the autostainer control program.

FIG. 20 illustrates the Slide Layout Map Screen of the autostainer control program.

FIG. 24 illustrates the Reagent Layout Map Screen of the autostainer control program.

DETAILED DESCRIPTION OF THE PREFERRED EMBODIMENT

A method and apparatus for automatically staining tissue specimens is disclosed. In the following description, for purposes of explanation, specific nomenclature is set forth to provide a thorough understanding of the present invention. However, it will be apparent to one skilled in the art that these specific details are not required in order to practice the present invention. For example, the present invention has been described with reference to staining of tissue specimens. However, the same techniques can easily be applied to other types of slide preparation work.

The Autostainer Hardware

Figure 1A:
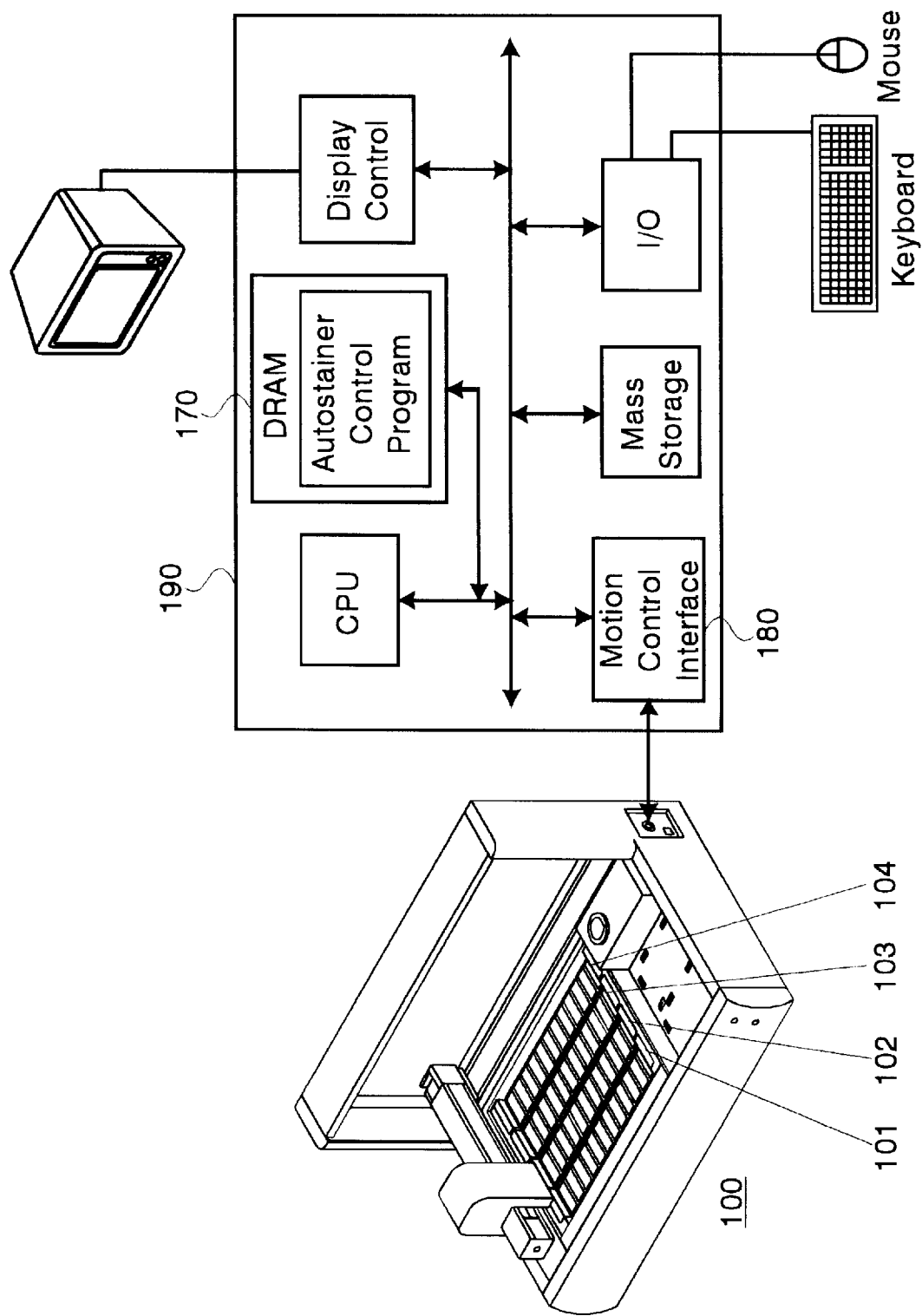
FIG. 1a illustrates a perspective view of the autostainer 100 apparatus.

FIG. 1a illustrates a perspective view of the autostainer 100 apparatus of the present invention. The autostainer 100 is used for staining tissue specimens that are placed onto glass slides. In the embodiment illustrated in FIG. 1a, there are four slide racks 101, 102, 103, and 104. Each slide rack is capable of holding twelve slides such that the autostainer 100 of FIG. 1a can perform operations on forty-eight slides at once.

The autostainer 100 of FIG. 1a has a robotic delivery system that delivers reagents, buffer solutions, and air to the glass slides. The robotic delivery system is controlled by a motion control interface card 180 in a personal computer system 190. The personal computer system 190 runs an autostainer control program 170 that sends control commands through the motion control interface 180 to control the robotic delivery system.

Figure 1B:
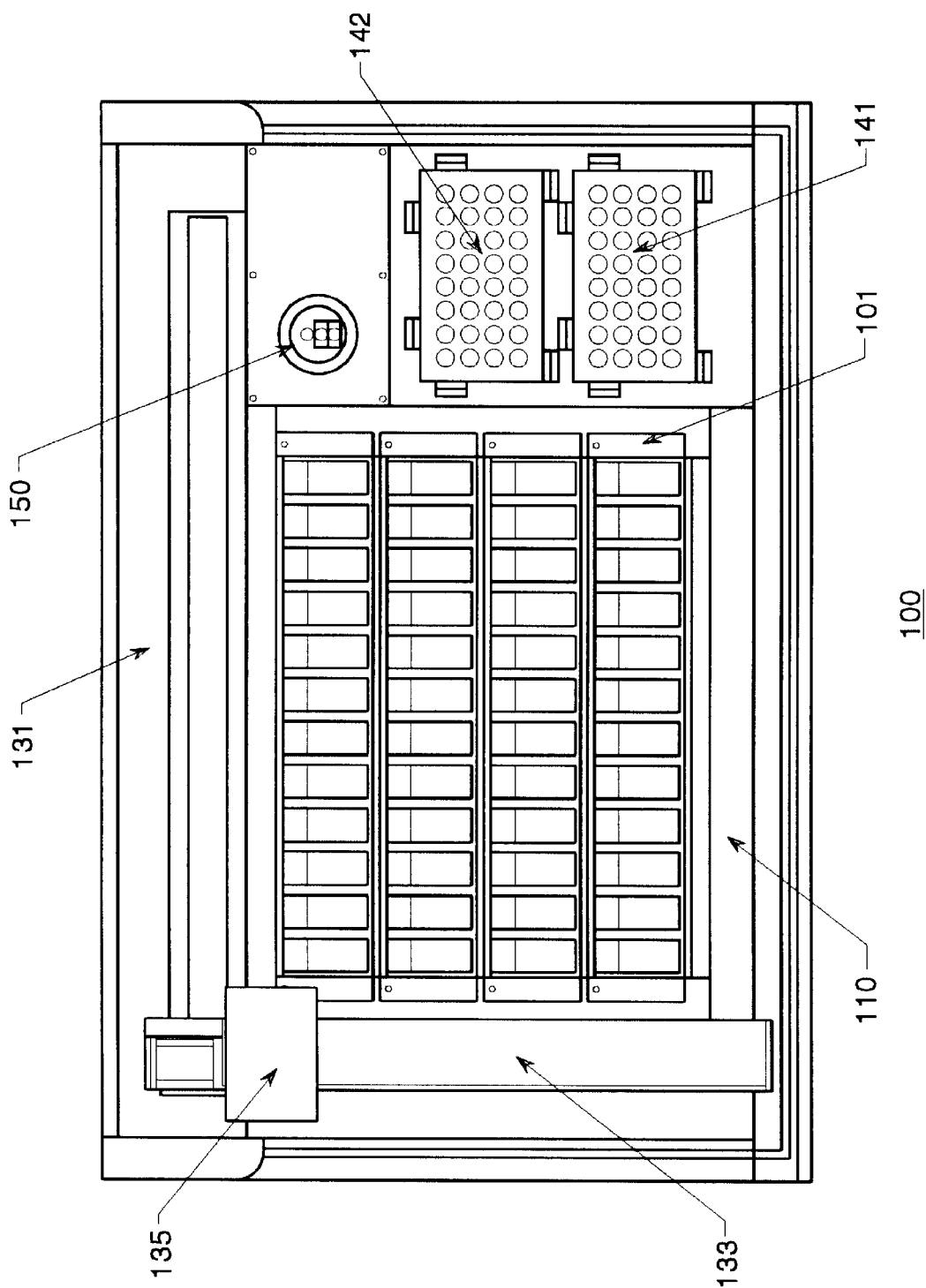
FIG. 1b illustrates a top view of the autostainer 100 apparatus.

FIG. 1b illustrates a top view of the autostainer 100. Referring to FIG. 1b, the robotic delivery system of the autostainer 100 consists of an X axis mechanism 131, a Y axis mechanism 133, and a Z head 135. The Z head 135 has a Buffer tube for dispensing buffer rinse solution, a blow nozzle to blow air onto slides, and a probe for picking up reagents that will be placed onto the glass slides. The various reagents are stored in the reagent racks 141 and 142.

To prevent contamination, the probe is cleaned in a reagent probe wash bin 150 between the use of different reagents. The wash bin 150 has three different receptacles that are used in three stages. The first hole is used to rinse the inside of the probe by forcing buffer rinse solution through the inside of probe and down into a first drain receptacle. The second receptacle is used to clean the outside of the probe by forcing buffer rinse solution through the inside of probe while the probe is in the tightly confined second receptacle such that the buffer solution is force upward on the outside of the probe. Finally, the probe is placed into a third receptacle and air is forced through the probe to clean out the buffer rinse solution.

Figure 2:
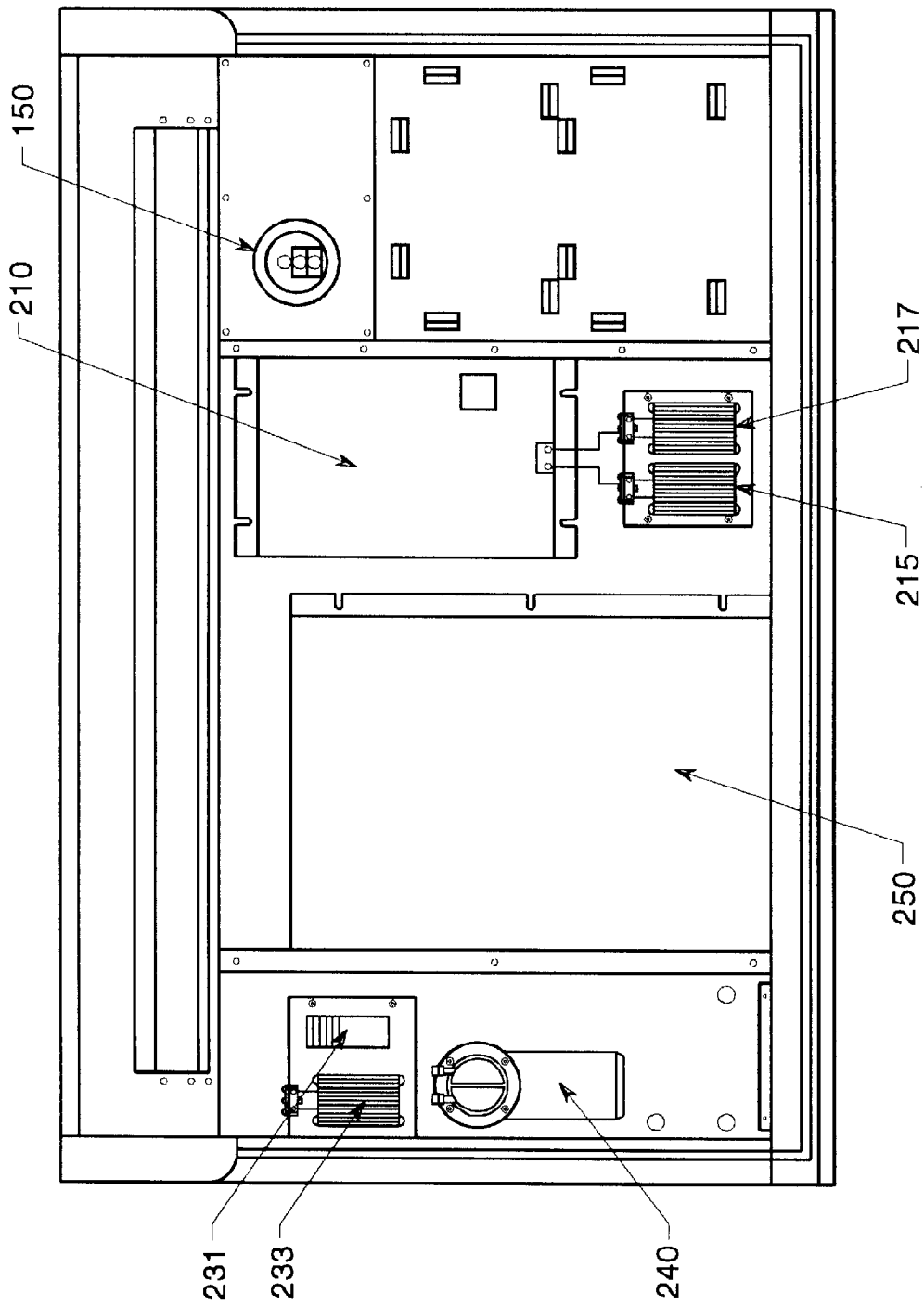
FIG. 2 illustrates a cut-away top view of the internal components of the autostainer 100 apparatus.

Beneath the slide racks of the autostainer 100 is a sink assembly 110. The sink assembly catches the reagents and buffer rinse solution that drips off the slides. FIG. 2 illustrates a cut-away top view of the internal components of the autostainer 100 apparatus. As illustrated in FIG. 2, a waste reservoir 210 that sits beneath the sink assembly collects the waste. The waste is pumped out of the waste reservoir 210 using a first waste pump 215 or a second waste pump 217. Two different waste pumps are used such that one waste pump is used to remove nonhazardous waste and the other waste pump is use to remove hazardous waste.

Several other components are also located inside the autostainer. Referring to FIG. 2 a buffer valve 231 and a buffer pump 233 are used to provide buffer rinse solution to the Z head assembly. An air compressor 240 is used to provide compressed air to the Z head assembly. An electronic controller box 250 stores a set of electronic components including the stepper motor drivers for the X, Y, and Z axes.

Autostainer Slide Racks

The slide racks for the autostainer of the present invention have been designed for optimum performance. FIG. 3a illustrates a top view a slide rack that is used in the autostainer. The slide rack 300 has twelve slide positions 310 such that the slide rack 300 can hold twelve slides. The slides may be standard U.S. or international sized slides. The slide rack can be carried using the handles 330 on each end of the slide rack 300. FIG. 3b illustrates a front view of the slide rack 300.

Figure 3C:
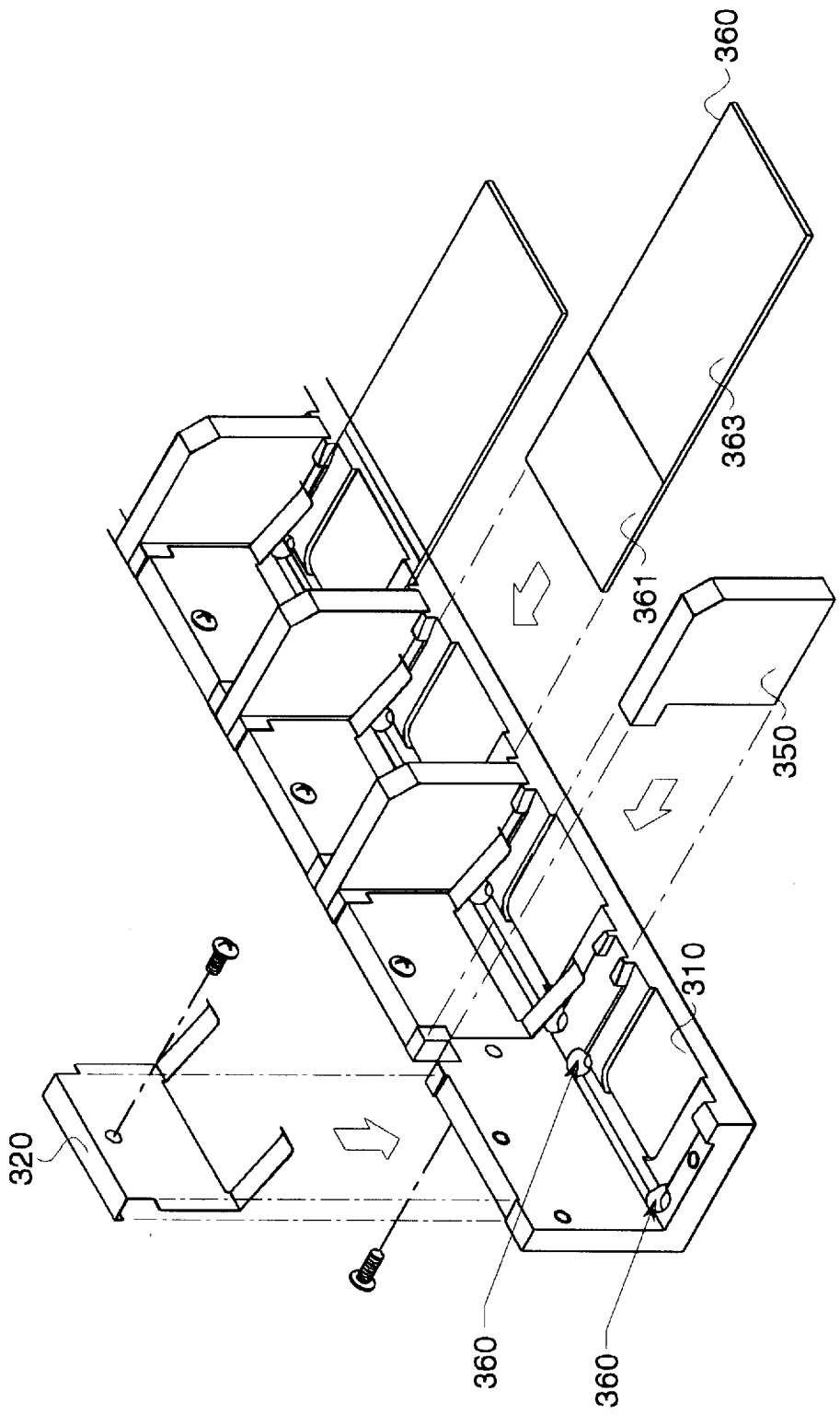
FIG. 3c illustrates a close-up perspective view of a slide rack for the autostainer.

FIG. 3c illustrates a close up view of four slide positions on a slide rack. Each position is shaped to accept a standard U.S. or an international sized slide 360. To hold the slide 360 in place, each slide position includes a stainless steel spring clip 320. The spring clip 320 is wide enough to accommodate common bar coding designations. The stainless steel spring clip 320 suspends the slide 360 by the frosted name section 361 of the slide 360. Since the slide 360 is held only in the frosted region 361 of the slide, the slide rack 300 does not interfere with the specimen or any of the applied reagents. Specifically, since there is no contact with the specimen area (the nonfrosted area), there is no capillary effect observed in prior art systems that draws off the reagent. Each slide position 310 is separated from the next slide position by a divider 350. The divider 350 prevents reagent or buffer from one slide overflowing onto an adjacent slide. Each slide position 310 includes two drain holes 360 for draining excess buffer rinse solution that may reach the areas where the slide is clipped to the slide rack.

Z Head Assembly

Figure 4B:
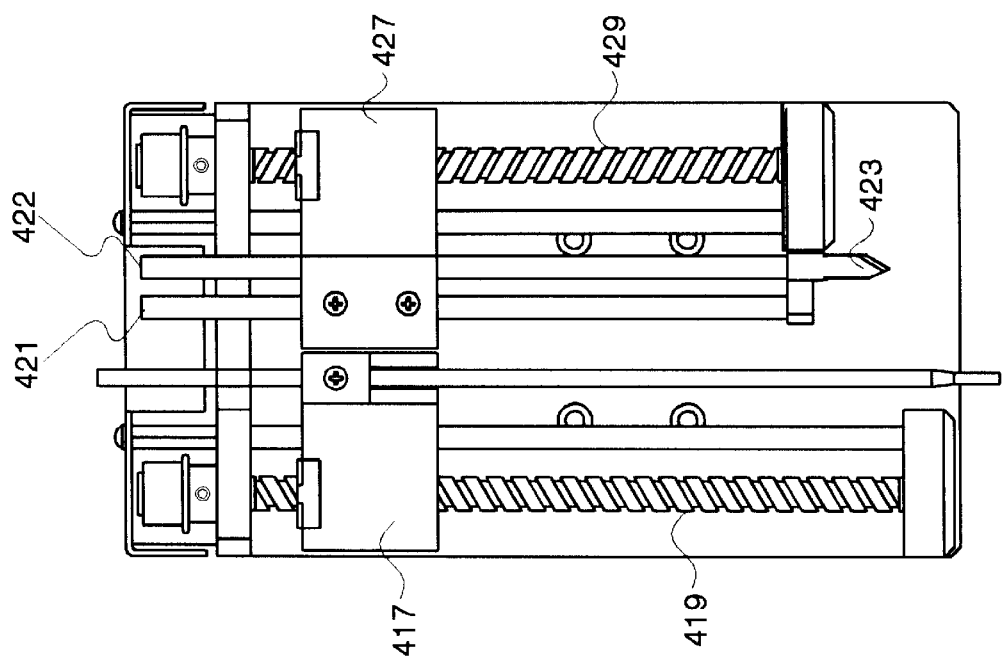
FIG. 4b illustrates a front view of the Z head assembly for the autostainer.
Figure 4A:
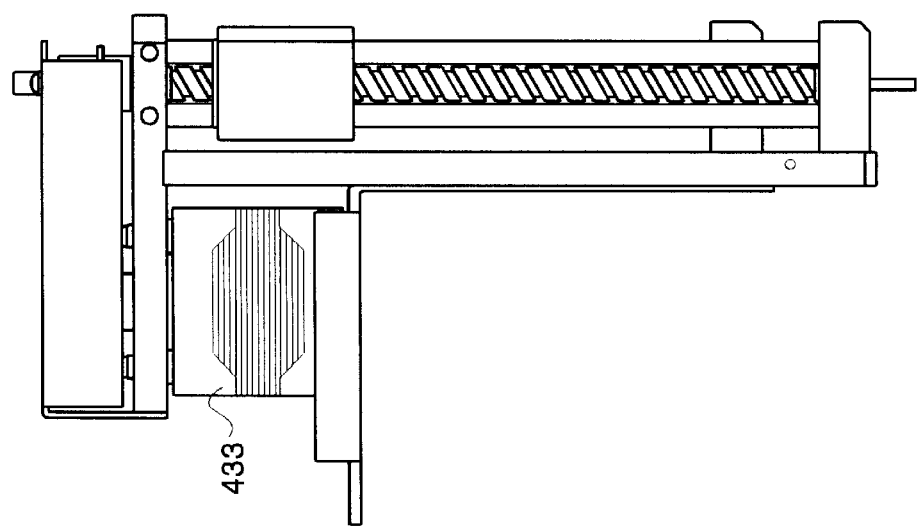
FIG. 4a illustrates a side view of the Z head assembly for the autostainer.

Referring back to FIG. 1b the autostainer 100 has a Z head assembly 135 that carries the buffer dispensing tube, the blow nozzle, and the reagent probe. FIGS. 4a and 4b illustrates a close-up of the Z head assembly. There are two different assemblies that move along the Z axis on the Z head: the reagent probe assembly and the air/buffer assembly.

The reagent probe assembly comprises the reagent probe 411, the reagent leadscrew nut block 417, and the reagent leadscrew 419. The reagent probe 411 is Teflon coated. The Teflon coating protects the stainless steel probe from corrosion and prevents reagent from sticking to the inside and outside walls of the probe. The reagent probe 411 includes custom circuitry that allows the reagent probe 411 to sense liquid levels. Since the reagent probe 411 can sense liquid levels, the probe goes into reagent vials only deep enough to obtain the desired amount of reagent. By only going deep enough to obtain the desired amount of reagent, the amount of contamination of the outside of reagent probe 411 is kept to a minimum. Furthermore, since the reagent probe 411 can sense liquid levels, it can determine if there is enough reagent in a vial to complete a staining run. This will be described in greater detail later.

The air/buffer assembly comprises the buffer tube 421, the air tube 422, the air nozzle 423, the air/buffer leadscrew nut block 427, and the air/buffer leadscrew 429. Since the reagent probe assembly and the air/buffer assembly are used independently, both assemblies can be driven the same stepper motor driver 433. The entire Z Head assembly is constructed in a modular form such that it can be replaced as a single unit.

Autostainer Air Nozzle

The Air nozzle on the Z head 135 of the autostainer has been designed to uniformly distribute air across the surface of a glass slide such that an optimal amount of residual buffer solution remains to keep the specimen hydrated. This allows for accurate consistent staining. FIGS. 5a through 5h illustrate the Air nozzle. FIG. 5d illustrates a cut-away side view of the air nozzle. The air nozzle has an air shaft 511, a well 513, and a nozzle slit 521. The nozzle slit forms a narrow opening when the nozzle lip 515 is coupled to the nozzle. The well 513 disperses the air such that uniform air flow is delivered out of the nozzle slit opening. The distribution angle of the nozzle allows the Z head to be narrower than prior art systems. Since the Z head is narrower, the slides can be grouped closer together such that the entire footprint of the autostainer has been reduced.

Autostainer Control and Programming

As stated in the previous section, the autostainer 100 is controlled by a personal computer system 190. In a present embodiment, the personal computer system 190 is a standard IBM compatible personal computer system running the Windows 95 operating system. The personal computer system 190 stores an autostainer control program 170 that is run when a user wishes to operate the autostainer 100.

The autostainer control program 170 is a sophisticated control program that implements many security, autoprogramming, control, and logging features. To fully describe the autostainer control program 170, this document will step through a sample use of the autostainer 100.

Autostainer Control Program Initialization

Figure 6:
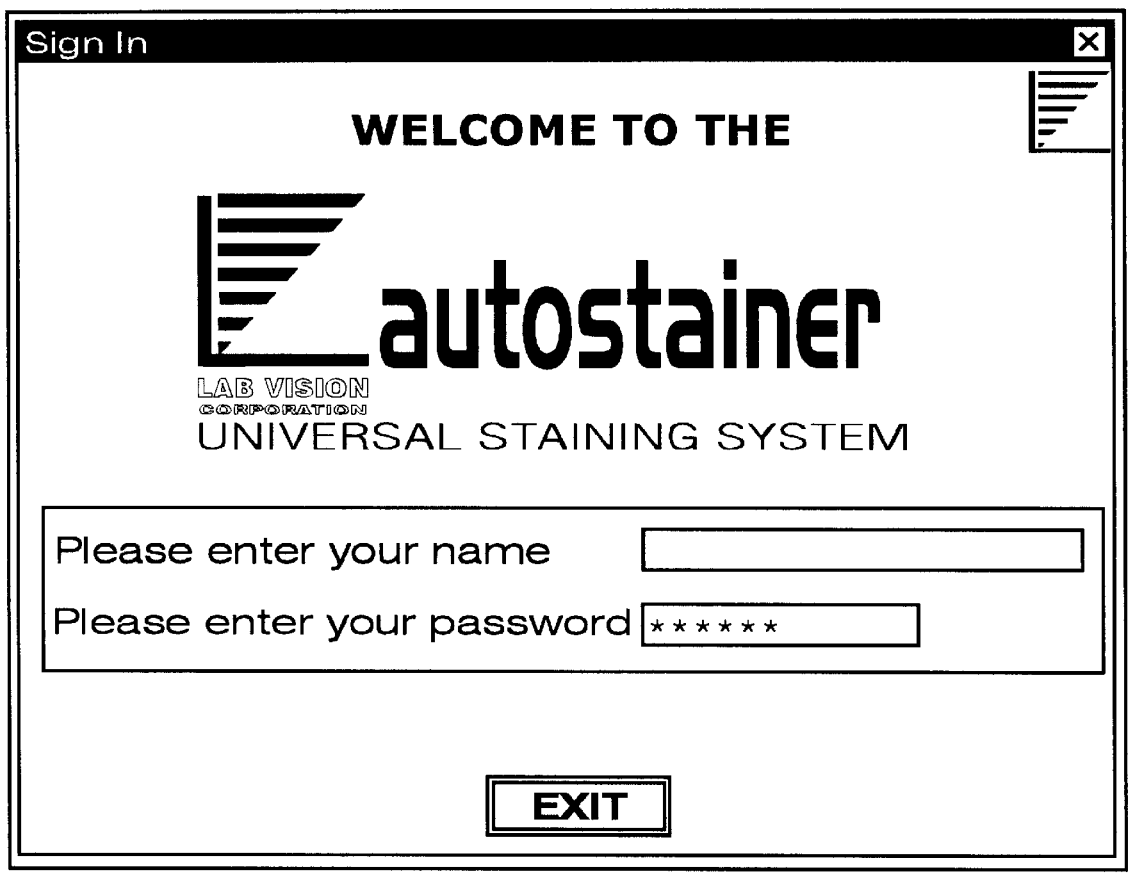
FIG. 6 illustrates the Sign-In Screen of the autostainer control program.
Figure 7:
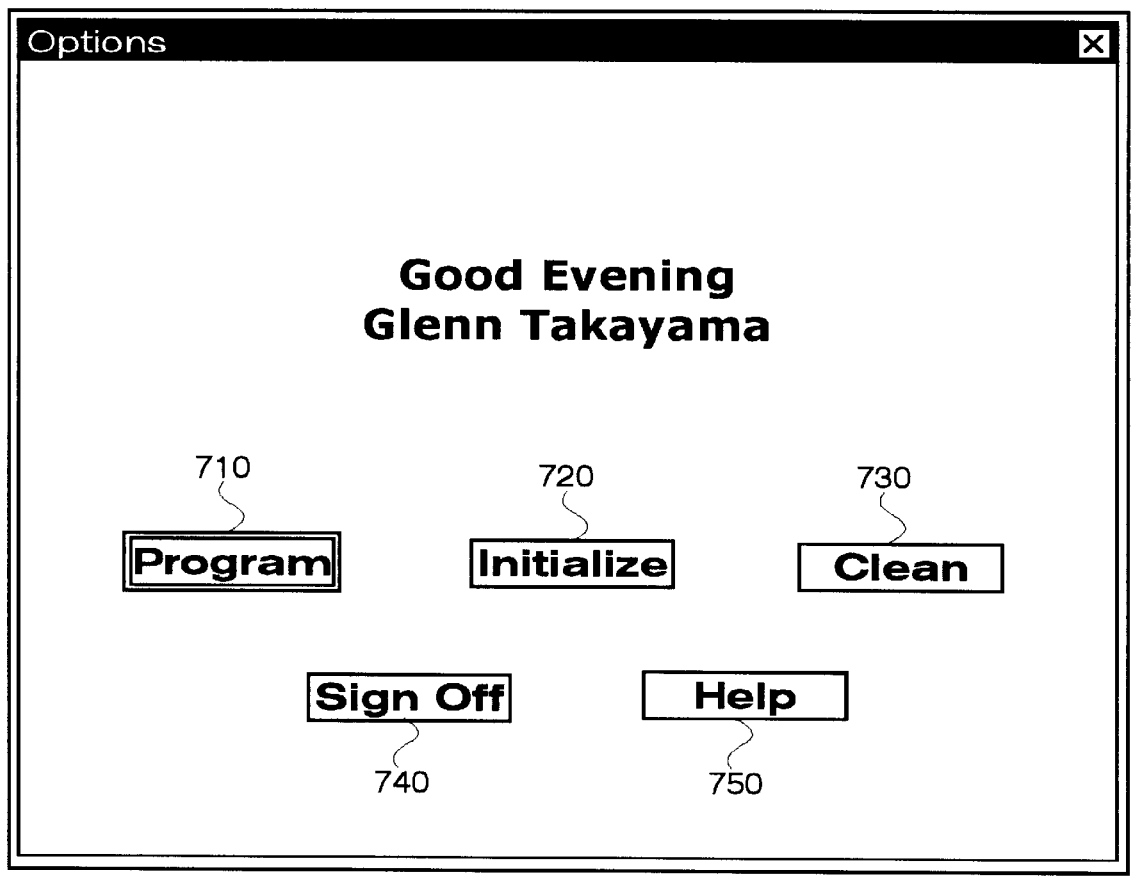
FIG. 7 illustrates the Options Screen of the autostainer control program.

When a user first runs the autostainer control program 170, a sign-in screen is displayed as illustrated in FIG. 6. The user enters a factory preloaded user name and password. After the factory preloaded user name and password have been entered, an option screen is displayed as illustrated in FIG. 7.

The option screen displays a set of functions that the user may select such as programming the autostainer for a run (program 710), initializing the autostainer control program (Initialize 720), cleaning the autostainer (clean 730), signing off (SignOff 740), and displaying help information (help 750). To initialize the autostainer control program 170, the user selects Initialize 720.

Figure 8:
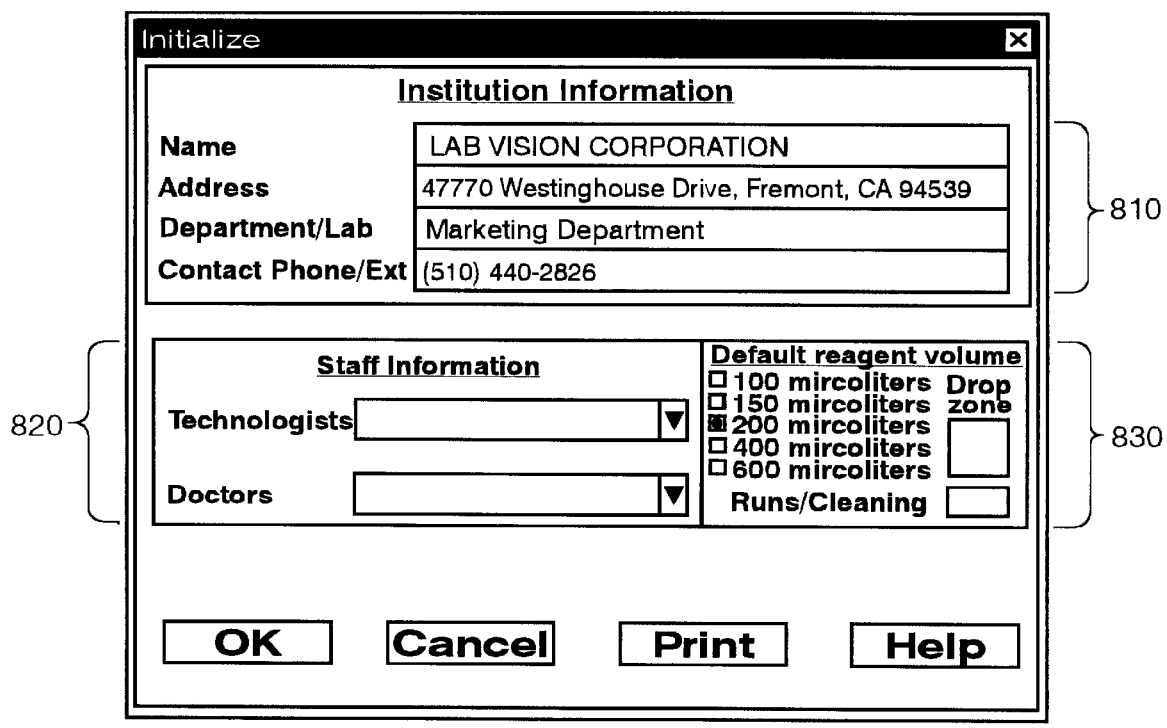
FIG. 8 illustrates the Initialize Screen of the autostainer control program.

After selecting the Initialize 720 button on the options screen, the Initialize screen is displayed as illustrated in FIG. 8. The initialization screen allows the user to enter information about the institution that will be using the autostainer in institution information area 810. Below the institution information area 810 is a staff information area 820.

The staff information area 820 allows an entry to be created for each user that will use the autostainer 100. The staff information area 820 allows both Doctors and technologists to be entered. Each user entry includes a user name, a user password, and a security level. The user name and password are used during the sign in process. The security level is used to limit access to features of the autostainer control program.

Finally, the Initialize screen allows a few autostainer operation parameters to be set. In the embodiment of FIG. 8, the parameter area 830 allows the user to specify the default reagent volume amount, the default reagent drop zone, and the number of runs allowed between cleanings.

The default reagent volume specifies the amount of reagent that will be used for all steps in any staining protocol. However, the default reagent volume can be overridden by specifically programming a different amount as will be described later. The default reagent drop zone specifies the default location where reagent will be applied to the slides. The default reagent drop zone can be overridden on the Slide Layout Map Screen of FIGS. 19 and 20 as will be described later.

The number of runs allowed between cleanings specifies how many times the autostainer may be used between maintenance cleanings. When the specified number of runs have occurred, a user will be notified that a cleaning cycle should be run at the options screen.

Creating a Staining Run

To run the autostainer, a user signs in with her user name and password as previously described with reference to FIG. 6. Then, at the option screen displayed in FIG. 7, the user selects the program button 710. After the selecting the program button 710, a blank Program Staining Run Screen is displayed as illustrated in FIG. 9a.

The Program Staining Run Screen is the central screen used to program a staining run. The Program Staining Run Screen displays a grid the steps that will be performed on each slide. The rows of the grid list the slides that will be stained. The columns of each row in the grid contain the patient name & case number, the Doctor name, and then all the steps that will be performed on that slide (row). The list of steps that will be performed on a slide are referred to as a "protocol."

Several pull-down menus are available on the top of the program staining run screen including "File" and "Edit." The File pull-down menu allows the user to create a new staining run program, open an old staining run program, save the current staining run program, and print the current staining run program. The Edit pull-down menu displays a list of all the available reagents that can be edited. To edit a reagent, the user selects the reagent in from the Edit pull-down menu and then an appropriate Edit reagent list screen will be displayed. The editing of reagents will be explained later. The Edit pull-down menu also lists a "Detection Kit" item. If the Detection Kit item is selected, then the Detection kit lot maintenance screen is displayed. The Detection kit lot maintenance screen allows detection kits consisting of 2 or more reagents to be created.

Also available at the top of the program staining run screen is a "Copy" function. One or more steps in a protocol can be selected using the cursor control device and then the "Copy" function can be used to copy the steps. The user can then move the cursor to another slide row and "paste" the steps into that slide's protocol. Thus, by cutting and pasting similar steps, the programming time is decreased.

Beneath the grid of slide and protocol information are six buttons for accessing additional programming features. The Patient Info button 910 moves the user to a patient information screen in order to enter new or edit existing patient information. The Protocol Template button 920 moves the user to a Protocol Template Design Screen where new staining protocol template can be created or a stored protocol template retrieved. The Run button 930 is selected when the user is satisfied with the information in the program staining run screen and wishes to start the staining run. The Print button 940 request the user if she wants a hard copy print out of the programmed staining grid that is currently displayed or an immunohistochemical report (IHC) as illustrated in FIG. 9b. The user simply selects the hard copy that is desired. The Exit button 950 returns the user to the option screen as illustrated in FIG. 7 without saving the any programming. The help 960 button displays context sensitive help information.

The general procedure for programming a staining run is as follows: (1) enter the patient information for each slide; (2) Select an existing or create a new protocol for staining run; (3) Select the reagents that will be used in the staining run; and (4) Load the slides and reagents and start the run. Each step merits its own discussion.

1) Entering Patient Information

To enter patient information for a staining run, the user selects the Patient Info button 910 from the Program Staining Run Screen of FIG. 9a. This moves the user to the Patient Information Screen as illustrated in FIG. 10.

The Patient Information Screen has input areas to allow the user to enter a patient name, a patient case number, the number of slides for that patient, and the Doctor that requested the slides. After entering all this information for a first patient, the form is cleared and the user can enter information for a next patient. The four buttons on the bottom of the Patient Information Screen are used to perform various operations.

The Delete button 1020 is used to delete a patient entries or case entries. The user can delete a patient entry using the patient selector arrow 1011 to select a particular patient name and then click on the Delete button 1020 to delete the selected patient entry. The user can delete a particular case for a patient entry using the patient selector arrow 1011 to select a particular patient name, then using the case selector arrow 1081 to select a particular case number, and then click on the Delete button 920 to delete the selected case.

The Cancel button 1030 allows the user to cancel all the entered patient information. When a user selects the Cancel button 1030, the user returns to the Program Staining Run Screen and none of the entered patient information is saved.

The Help button 1040 can be selected to receive context sensitive help information. Thus, the Help button 1040 displays help information about the Patient Information Screen.

After entering all the desired patients, the user selects the Finish Entry button 1010 to return to the Program Staining Run Screen with the new patient information displayed. After entering all the patient information, the next step is to select an existing or create a new protocol for staining run. Thus, from the Program Staining Run Screen the user selects the Protocol Template button 920.

2) Creating A New Or Accessing An Existing Protocol Template

To select a protocol template for a staining run, the user selects the Protocol Template button 920 from the Program Staining Run Screen. This moves the user to the Protocol Template Design Screen as illustrated in FIG. 11.

Figure 11:
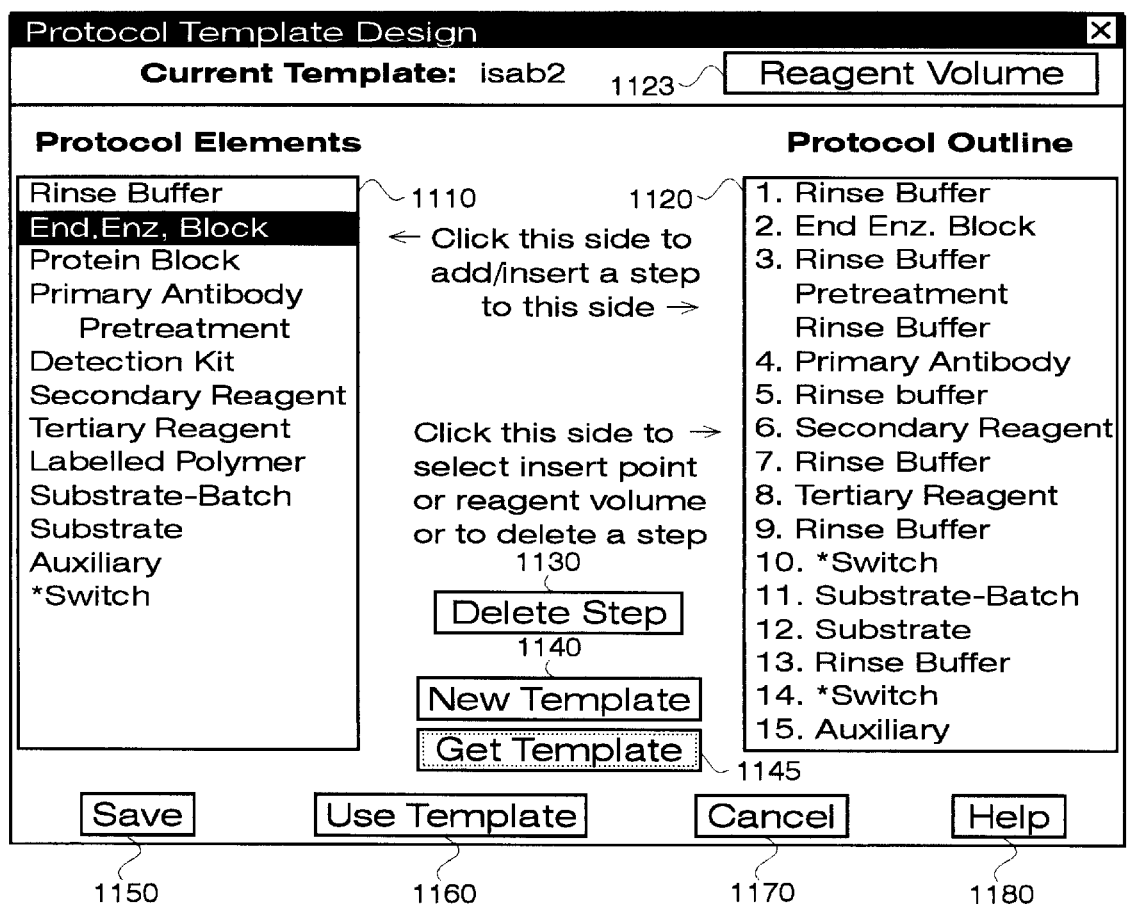
FIG. 11 illustrates the Protocol Template Design Screen of the autostainer control program.

The Protocol Template Design Screen of FIG. 11 is divided into two vertical columns. The left column is the Protocol Element column 1110. The Protocol Element column 1110 lists the various steps that can be used to create a protocol. The right column is the Protocol Outline column 1120. The Protocol Outline column 1120 lists the steps that have been selected for the current protocol.

The Protocol Template Design Screen enables the user to create staining protocol templates to be used in the staining runs. Protocol templates can be created and stored for future use. To create a protocol template, the user selects protocol steps from the Protocol Element column 1110 and moves them to the Protocol Outline column 1120.

The available protocol steps include: Endogenous Enzyme Block, Protein Block, Primary Antibody (and Pretreatment), Detection Kit, Secondary Reagent, Tertiary Reagent, Labeled Polymer, Substrate-Batch, Substrate, Auxiliary, Switch (Swtch), and Rinse Buffer. The specific reagents used during reagent steps are assigned to each slide from the Program Staining Run Screen as will be described in the next section.

The Rinse Buffer step consists of an air blow and rinse buffer wash cycle. The Rinse Buffer step should be programmed between all protocol template steps to remove reagents from the slides between the staining run steps. The default Rinse Buffer step can be replaced by a blow only step by clicking on the Rinse Buffer step droplet icon on the Program Staining Run Screen with the right mouse button. This replaces the droplet icon with a wind icon indicating a blow only.

The Substrate-Batch Protocol step allows unstable substrates that need to be prepared immediately prior to application. The Substrate-Batch Protocol step splits the staining run into two phases: a first phase prior to the application of the unstable substrate and a second phase batching all the steps starting with the unstable substrate application. The autostainer will stop after all the steps in the first phase and beep to indicated that the substrate should be prepared. The user then prepares the substrate and loads it into a designated position in the reagent rack. After the user has placed the unstable substrate into the designated position in the reagent rack, the user prompts the autostainer to continue the staining run.

The Switch (Swtch) step allows a user to indicate the switching of waste from one container to another. The Switch (Swtch) step is primarily used to separate hazardous waste from nonhazardous waste. A protocol template containing a switch step switches from the primary (nonhazardous) waste system to a secondary (hazardous) waste system. On the Program Staining Run Screen, the first Switch step will be displayed as a skull and crossbones to indicate a switch to the secondary (hazardous) waste system. The next Switch step will be displayed as a flowers icon to indicate a switch to the primary (nonhazardous) waste system. Accordingly, subsequent switch steps alternate between the secondary (hazardous) waste system and the primary (nonhazardous) waste system. Switch steps must always be preceded by a rinse step.

As illustrated in FIG. 11, the Protocol Template Design Screen has the following function buttons: New Template 1140, Get Template 1145, Use Template 1160, Delete 1130, Reagent Volume 1123, Save 1150, Cancel 1170, and Help 1180. The New Template 1140 button clears the Protocol Outline column 1120 such that a new template may be created. The Get Template 1145 button displays a file requester box such that an existing template may be fetched. The Use Template 1160 button installs the protocol template displayed in the Protocol Outline column 1120 and returns to the Program Staining Run Screen. Delete 1130 deletes a highlighted step from the Protocol Outline column 1120. The Reagent Volume 1123 button assigns a reagent dispense volume to a highlighted step (or all the steps if a specific step is not highlighted) in the Protocol Outline column 1120. The Save 1150 button saves the Protocol template currently displayed in the Protocol Outline column 1120 into a file. The Cancel button 1170 allows the user to cancel all the entered information and returns the user to the Program Staining Run Screen. The Help button 1180 can be displays context sensitive help information.

After selecting the Save 1150 button, the Use Template 1160 button, or the Cancel button 1170 the user is returned to the Program Staining Run Screen.

3) Selecting the reagents that will be used in the staining run

When the user returns to the Program Staining Run Screen after selecting a protocol template, the first reagent step to be programmed will be flashing. There are two different ways of assign reagents to the slides. The first method is to edit the reagents for a slide by selecting the slide. The second method is to select a reagent box on the Program Staining Run Screen and an appropriate reagent list will be displayed such that a reagent may be selected.

Figure 12:
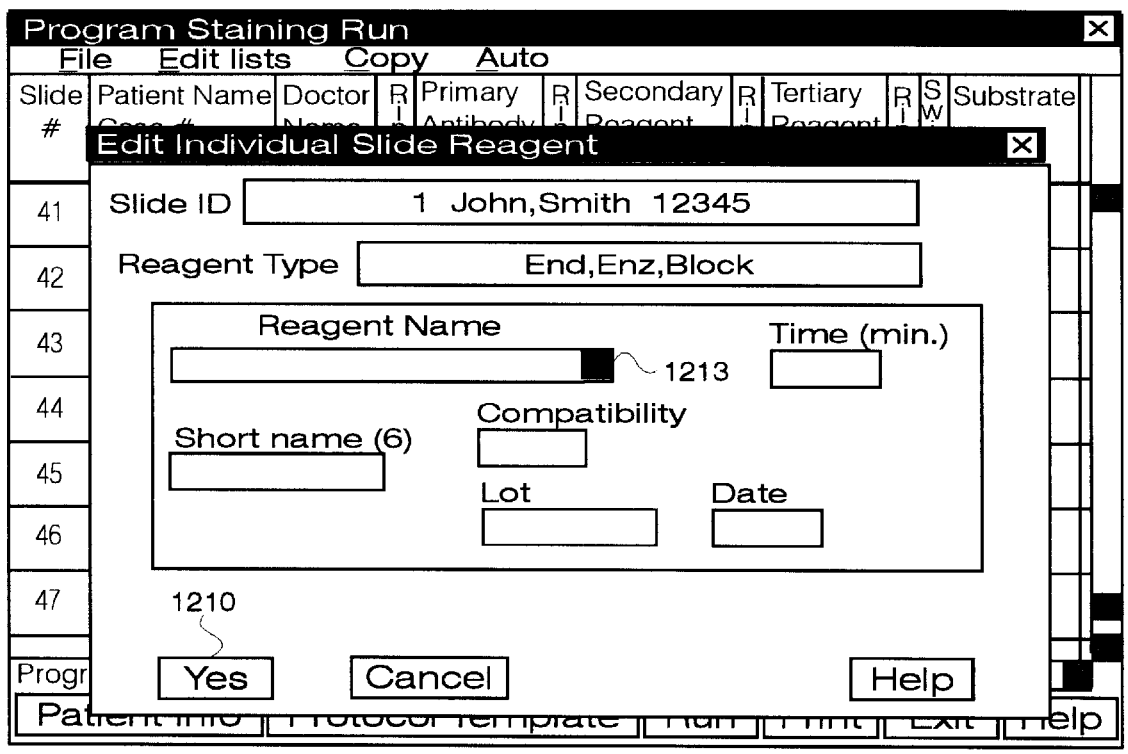
FIG. 12 illustrates an Edit Individual Slide Reagent Screen of the autostainer control program.
Figure 13:
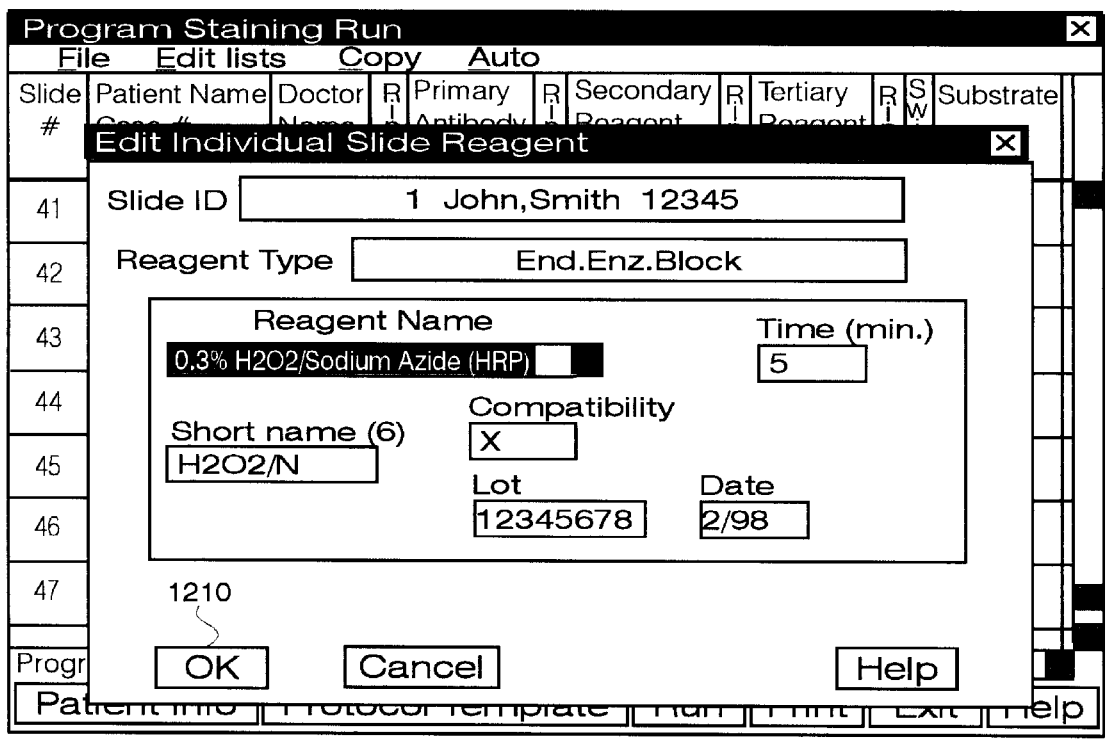

To edit an individual slide, a user can select a slide tile and then click on the "Edit Slide" item displayed at the top of the reagent list. This brings up the Edit Individual Slide Reagent Window. For example, FIG. 12 illustrates the Edit Individual Slide Reagent Window for the Endogenous Enzyme Block of Slide 1. To select a reagent, the user can use the down arrow 1213 in the reagent name field to select the desired reagent. FIG. 13 illustrates how the Edit Individual Slide Reagent Window appears after the H202/N reagent has been selected.

Using the Edit Individual Slide Reagent Window, slide specific edits can be made. No edits made on the Edit Individual Slide Reagent Window will affect the reagent file. However, after the user selects the "OK" button 1210, the user will be asked if she wants the same reagent applied to all the unprogrammed slides as illustrated in FIG. 14. If all or most of the slides are undergoing the same treatment, the user should select the "yes" button 1420 such that the autostainer program fills in the selected reagent for the same step in the remaining unprogrammed slides. If the majority of the slides have different protocols, the user should select the "no" button 1430. The remainder of the reagents for the slide can be edited in the same manner.

The other method of editing reagents is to select a particular reagent tile from the Program Staining Run Screen grid. This will bring up an appropriate list of reagents that may be selected. For example, FIG. 15 illustrates a Detection Kit tile for slide 3 highlighted such that an appropriate list of Detection Kits is displayed in a pop-up window 1510. The user simply selects the desired Detection Kit from the pop-up window 1510. Note that one of the Detection Kits in the list is "None" such the tile may be cleared. After selecting a reagent, a window will ask the user if the same reagent should be assigned to the remaining unprogrammed slides as explained above.

The users programs of all the reagent steps using the two methods described above. To reduce the work involved, the user can use the "Copy" command from the menu to copy protocol and reagent information from slides that have already been programmed into unprogrammed slide rows.

The autostainer of the present invention includes a compatibility check feature to prevent incompatible reagents from being used on the same slide. In a present embodiment there are two compatibility tests performed although more can be added in future versions. The first compatibility check tests the species reactivity compatibility of the primary antibody and the secondary reagent used. The second compatibility check tests the compatibility rules dictated by the enzyme used in the detection system. The following chart summarizes the current compatibility rules:

| Species Reactivity Compatibility Rules | | |
|---|---|---|
| Reagent Type | Description | Compatibility Code |
| First Compatibility Check: Species Compatibility | | |
| Primary Antibody | All monoclonal primary antibodies raised in mouse (e.g., mouse anti-human) | A |
| Primary Antibody | All polyclonal primary antibodies raised in rabbit (e.g., rabbit anti-mouse IgG) | B |
| Secondary Reagent | All secondary reagents (antibodies) compatible with monoclonal antibodies raised in mouse (e.g., biotinylated anti-mouse IgG) | A |
| Secondary Reagent | All secondary reagents (antibodies) reacting with polyclonal antibodies raised in rabbit (e.g., biotinylated anti-rabbit IgG) | B |
| Second Compatibility Check: Enzyme System Compatibility | | |
| Endogenous Enzyme Block | HRP-compatible | X |
| Endogenous Enzyme Block | AP-compatible | Y |
| Tertiary Reagent | HRP-labeled streptavidin | X |
| Tertiary Reagent | AP-labeled streptavidin | Y |
| Substrate | HRP-compatible substrates (i.e. DAB, AEC)) | X |
| Substrate | AP-compatible substrates (i.e. Fast Red, New Fuchsin) | Y |

When a user attempts to enter a reagent that is incompatible with a previously selected reagent, the Incompatible Reagent Warning Box is displayed as illustrated in FIG. 16. The Incompatible Reagent Warning Box asks the user if the incompatible reagent should be used. If the user selects "no" then incompatible reagent is erased. If the user selects, then the incompatible reagent remains.

Figure 17:
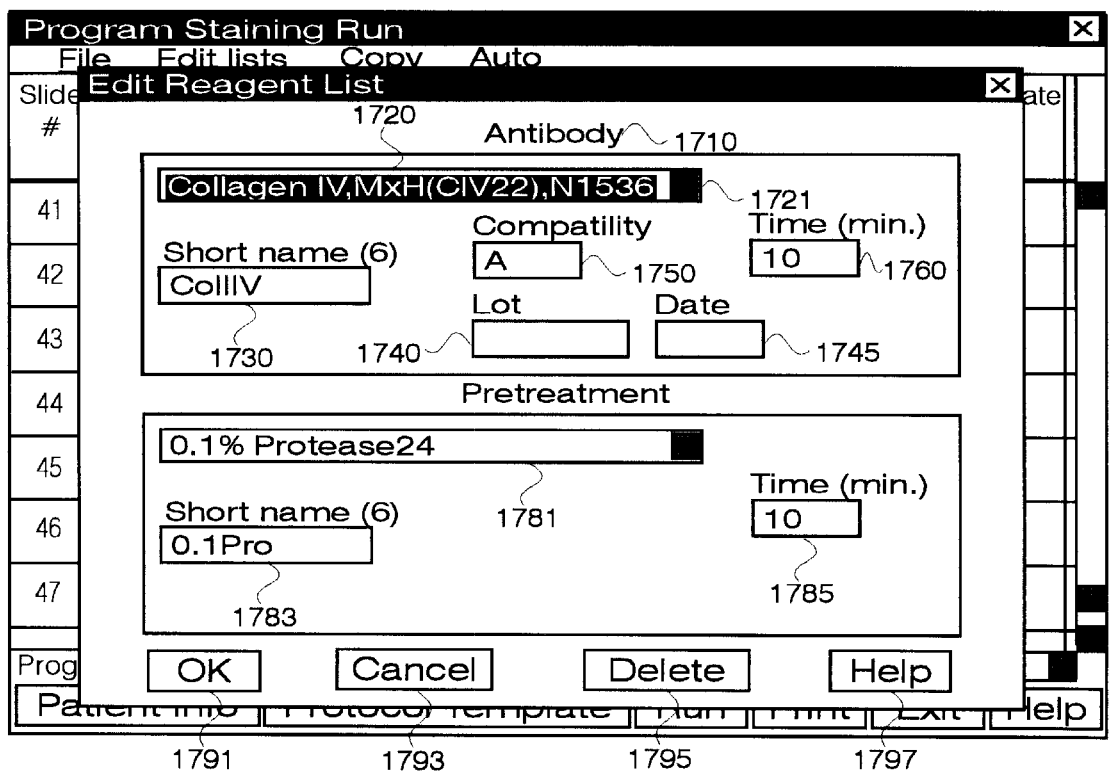
FIG. 17 illustrates the Edit Reagent List Screen of the autostainer control program.

To edit the actual reagents that are available for use, the user selects a reagent type from the Edit pull-down menu on the Program Staining Run Screen. The Edit pull-down menu displays the following reagents that can have their parameters modified: Endogenous Enzyme Block, Protein Block, Primary Antibody, Pretreatment, Secondary Reagent, Tertiary Reagent, Labeled Polymer, Substrate, and Auxiliary. When the reagent type is selected, such as the Primary Antibody reagent, the user is moved to the Edit Reagent List Screen as illustrated in FIG. 17.

At the top of the Edit Reagent List Screen is a title 1710 that lists the type of reagents that can be displayed. In the example of FIG. 17, the Collagen IV antibody of the Primary Antibody type of reagent is displayed. The remainder of the Edit Reagent List Screen displays the relevant information the particular reagent that is on the screen. The information includes: the reagent long name 1720, the reagent short (6 character) name 1730, a lot number 1740, an expiration date 1745, a compatibility code 1750, and an incubation time 1760. To edit the information, the user simply types in the desired field. In the particular case of the Primary Antibody reagent, the information about the corresponding pretreatment is also displayed including the pretreatment name 1781, the pretreatment short (6 character) name 1783, and the incubation time 1785. The information about the corresponding pretreatment can also be edited by typing in the desired field.

To select a different reagent of the type of reagent listed in the title 1710, the user uses the name selector arrow 1721 or moves the cursor to the reagent long name field and presses the down arrow key until the desired reagent is displayed. The user then hits Enter to obtain the information about that particular reagent. To delete the reagent that is current displayed, the user can select the Delete button 1795 at the bottom of the screen.

To return to the Program Staining Run Screen, the user selects the OK button 1791. To return to the Program Staining Run Screen without saving the changes that have been entered the user can select the Cancel button 1793. Context sensitive help is available by pressing the Help button 1797.

4) Selecting the reagents that will be used in the staining run

Once all the patient information has been entered, the desired slide protocols have been set up, and the desired reagents have been selected then the autostainer is ready to be operated. Thus, the user must physically load the slides and reagents. These steps will be described in the next section.

Autostainer Operation

Figure 19:
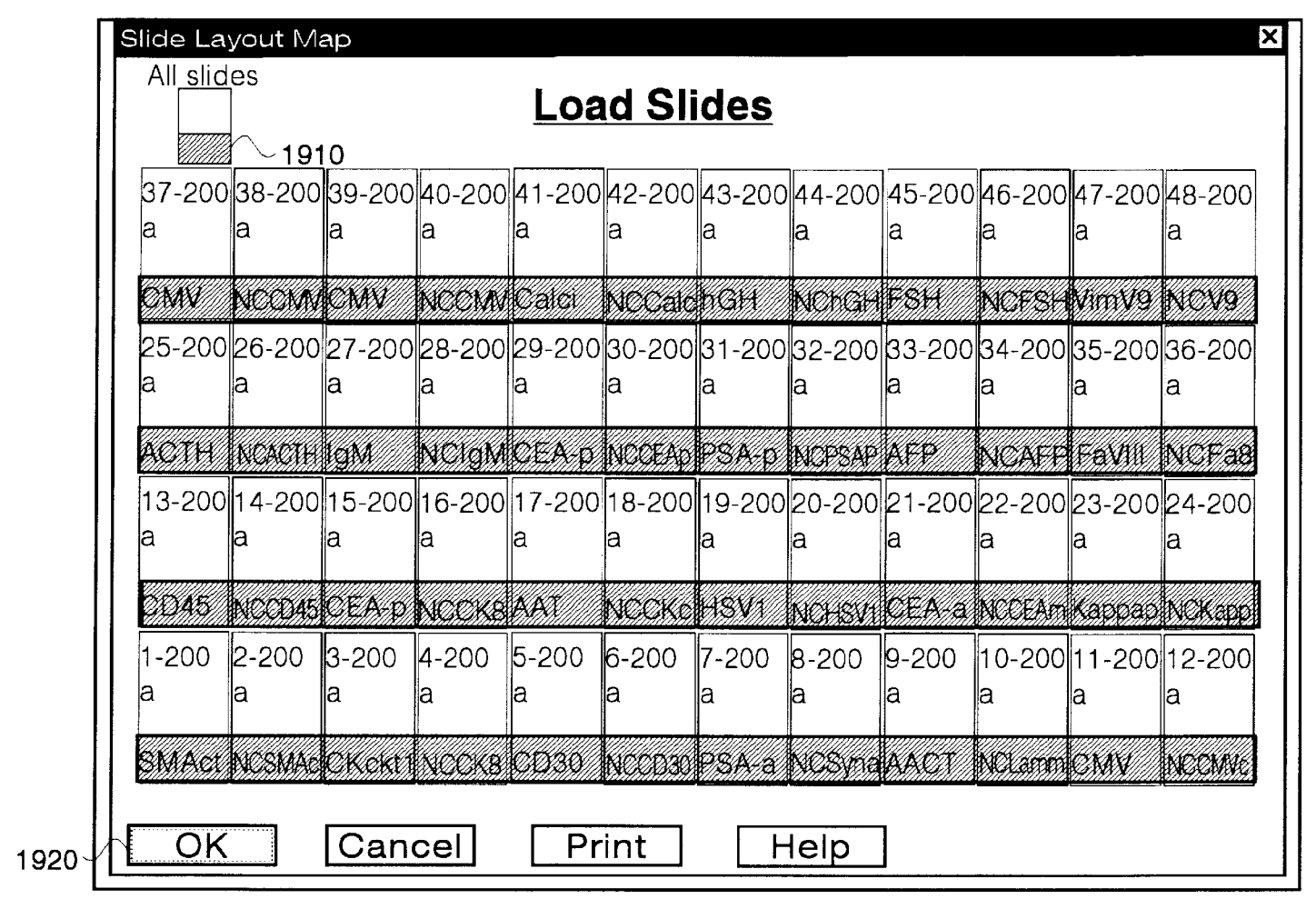

After the patient information, the slide protocols, and the desired reagents have been entered, the Program Staining Run Screen grid will appear as it does in FIG. 18. To begin the staining operation, the user selects the "Run" button at the bottom of the Program Staining Run Screen. The autostainer program will ask the user if the staining run program should be saved as illustrated in FIG. 18. After saving (or not saving) the programmed information, the user is moved to the Slide Layout Map Screen as illustrated in FIG. 19.

The Slide Layout Map Screen displays a grid of all 48 slides. Each slide is identified with the slide's slide number, the primary antibody abbreviation, the primary antibody volume, and the case number.

Figure 20:
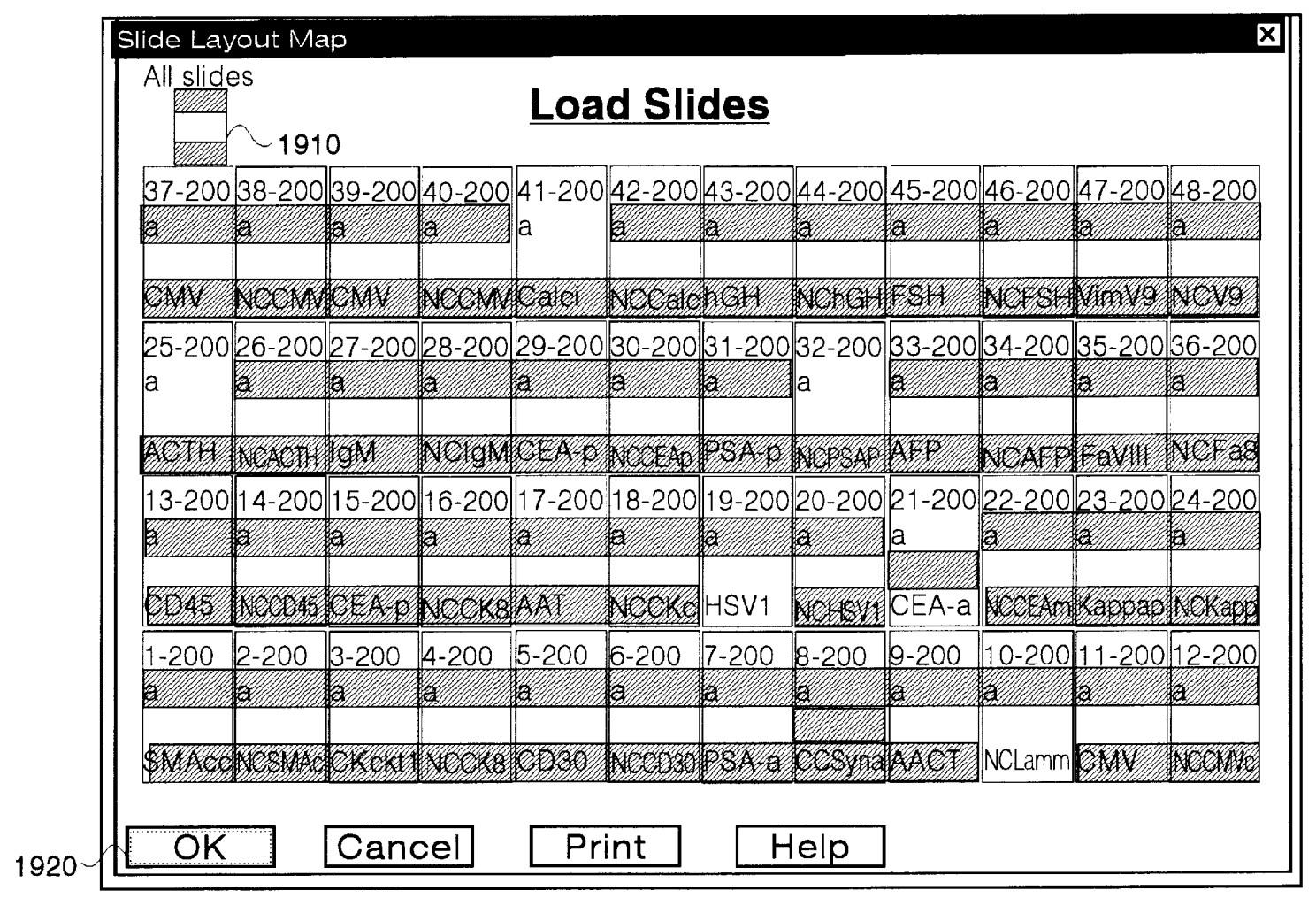

Each slide is also has a designation of where the reagent will be dispensed onto the slide. The non frosted zone of each slide is divided into three dispense zones. The default dispense location is set on the Initialization Screen of FIG. 8. To change the dispense location for all the slides, the user can select any of the three zones on an "All slides" icon 1910 in the upper left-hand corner. By toggling the a zone of the "All slides" icon 1910, all the slides on the Slide Layout Map Screen are affected. Furthermore, the dispense location for individual slides can be set by toggling the three sections of the individual slide representation. FIG. 20 illustrates the Slide Layout Map Screen after the top third of the "All Slides" icon 1910 has been toggled and several individual slides have been toggled.

The Slide Layout Map Screen allows the user to make a final check of the staining run. If the user is not satisfied, the user can select the Cancel button 1930 to return to the Program Staining Run Screen. The user can select the Print button 1940 to print the Slide Layout Map Screen. The Help button 1950 displays context sensitive help information.

If the user is satisfied with the contents of the Slide Layout Map Screen, then the user must load the slides into the autostainer as specified on the Slide Layout Map. After the has loaded the slides, the user selects the OK button 1920 to proceed. After the user selects the OK button 1920 on the Slide Layout Map Screen, the autostainer control program proceeds to calculate the most efficient dispensing pattern for performing the desired slide protocols.

Figure 21:
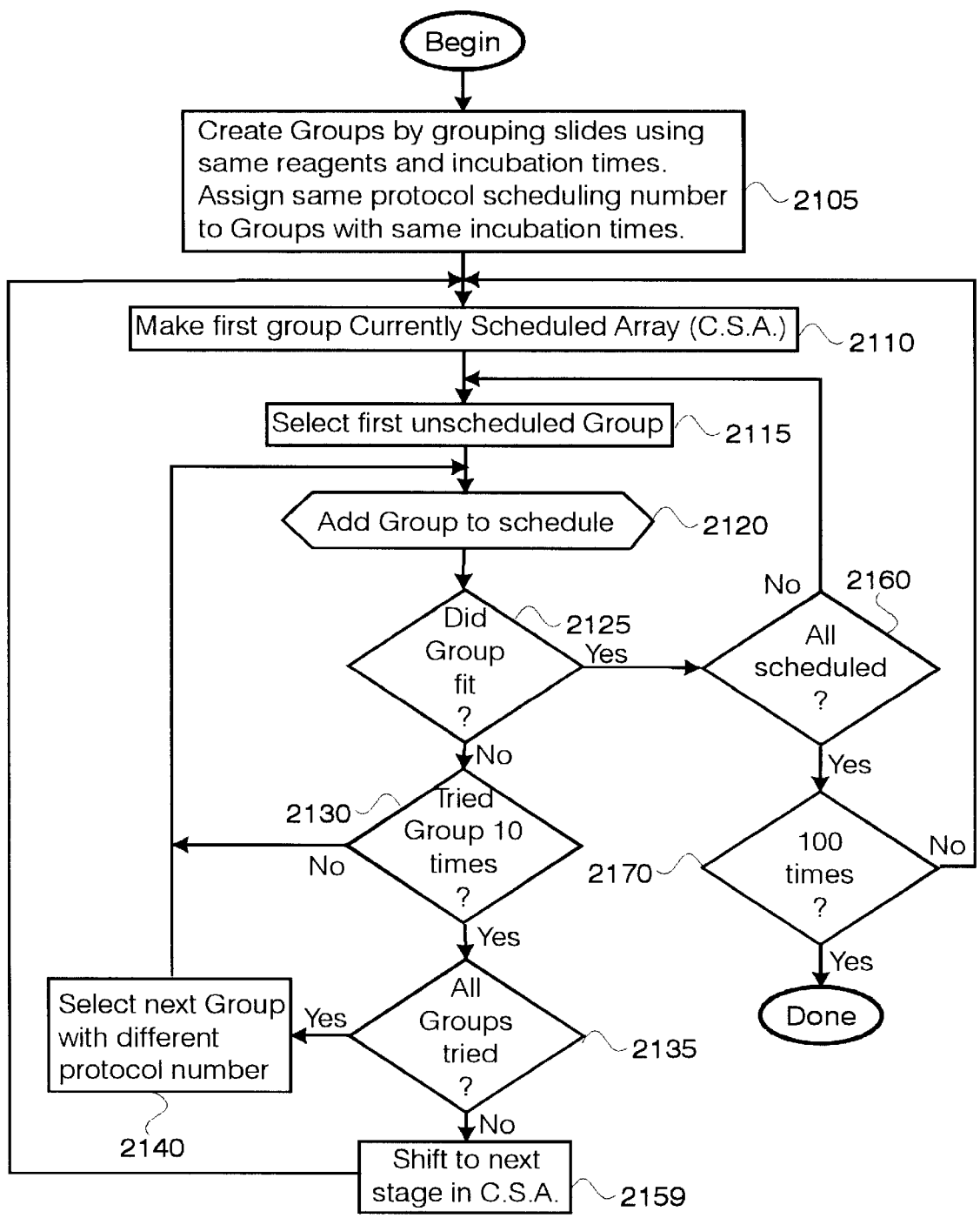
FIG. 21 illustrates a summary of the scheduling system of the autostainer control program.
Figure 22A:
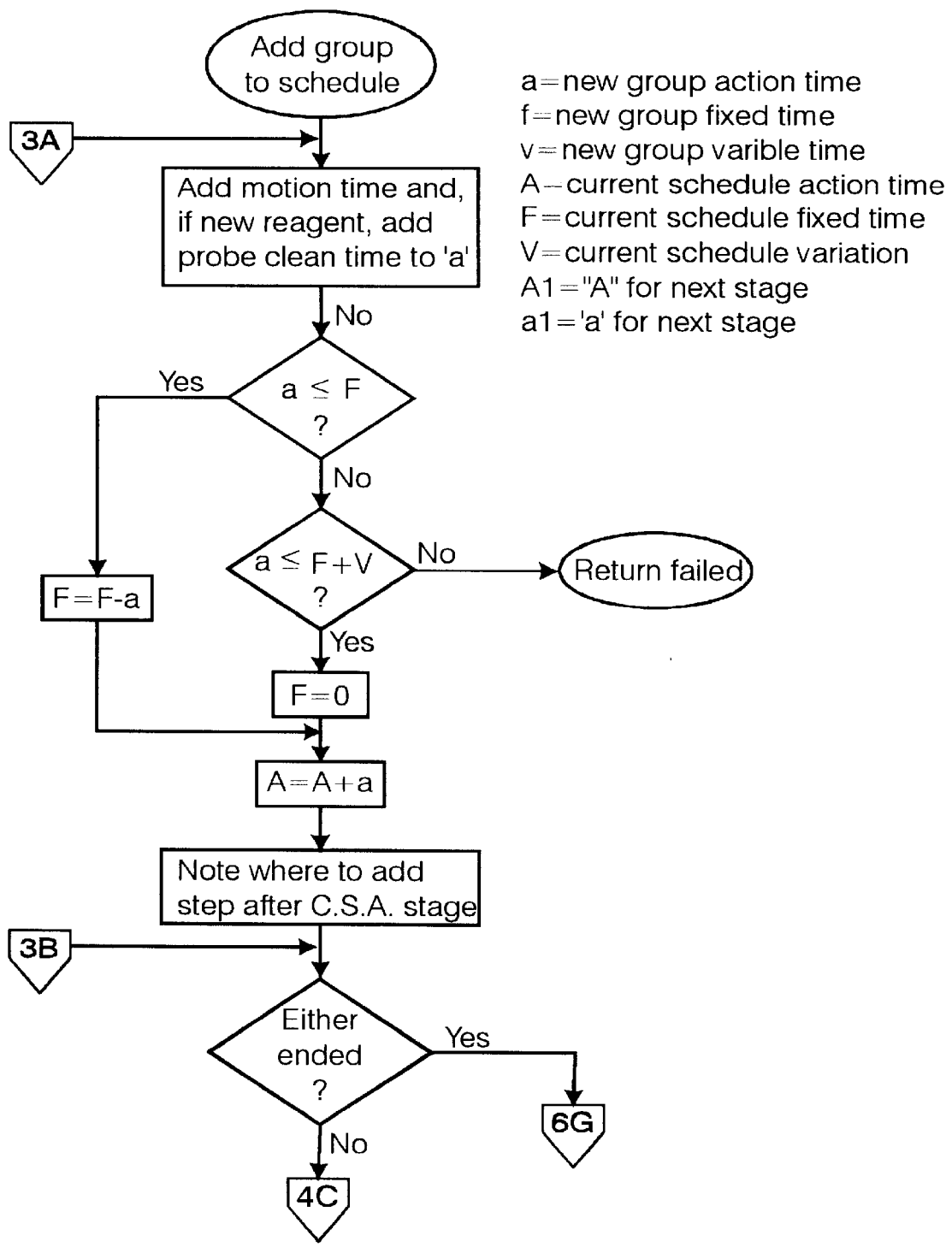
FIGS. 22a through 22d list the details of adding a new group to the Currently Scheduled Array.
Figure 22B:
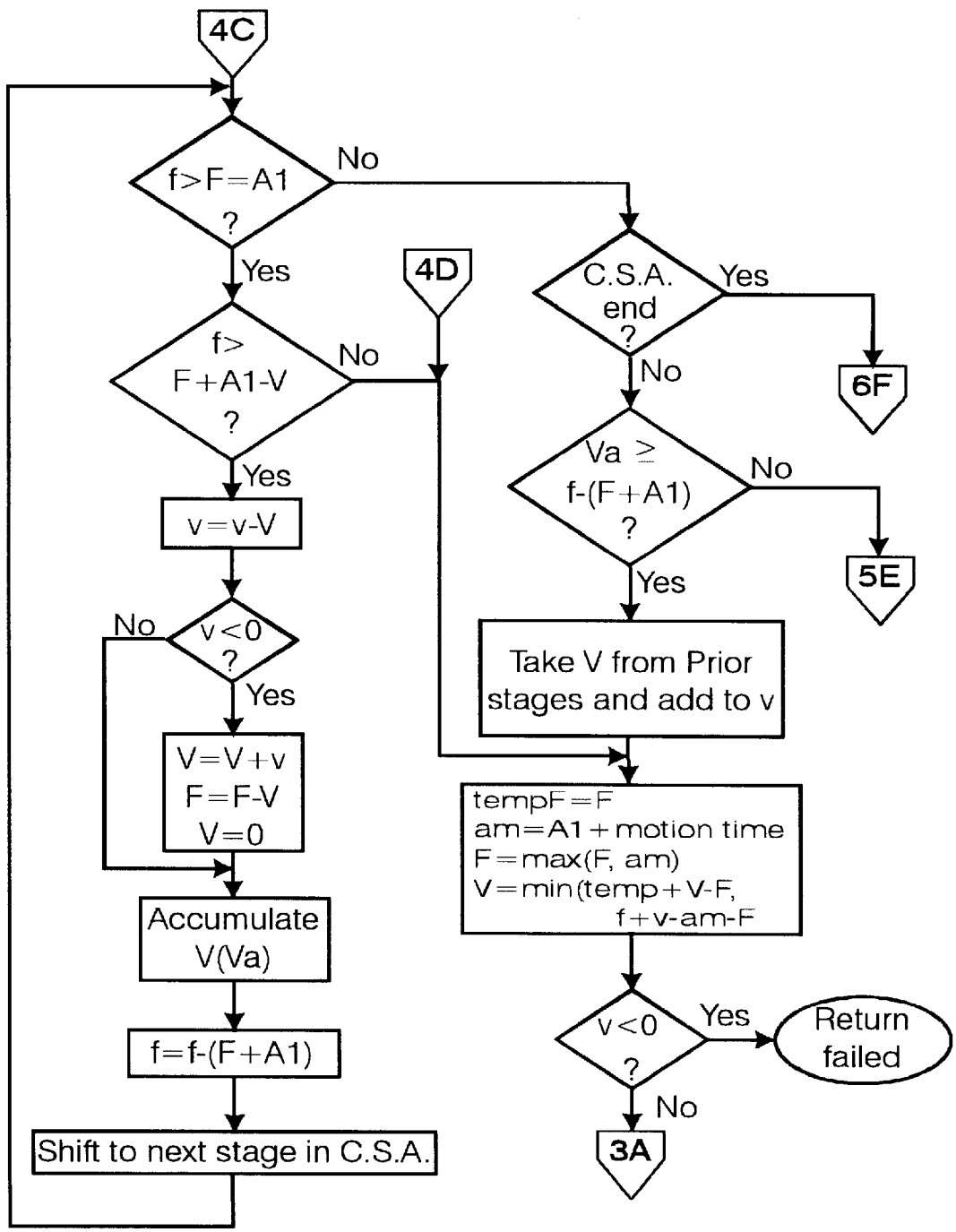
Figure 22C:
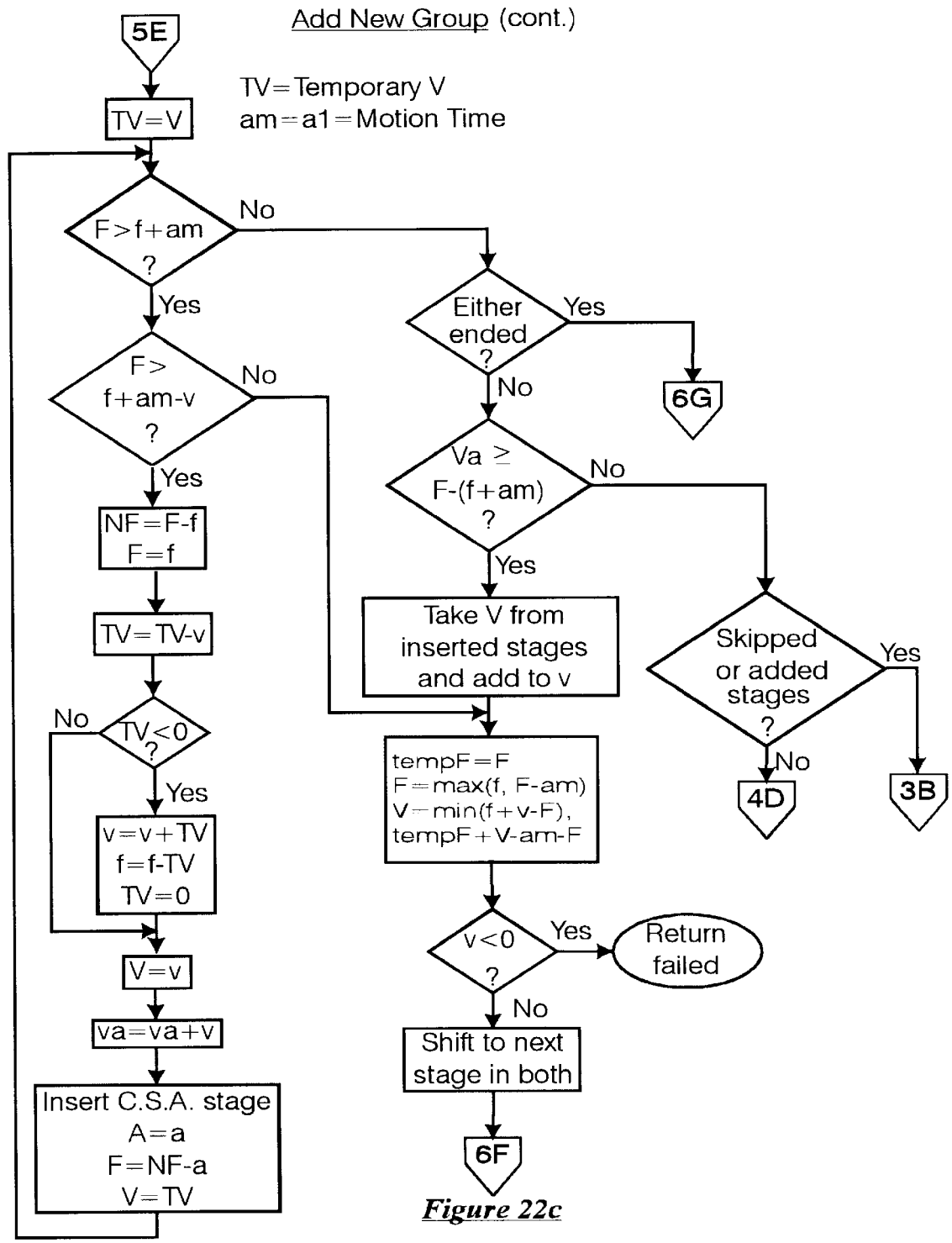
Figure 22D:
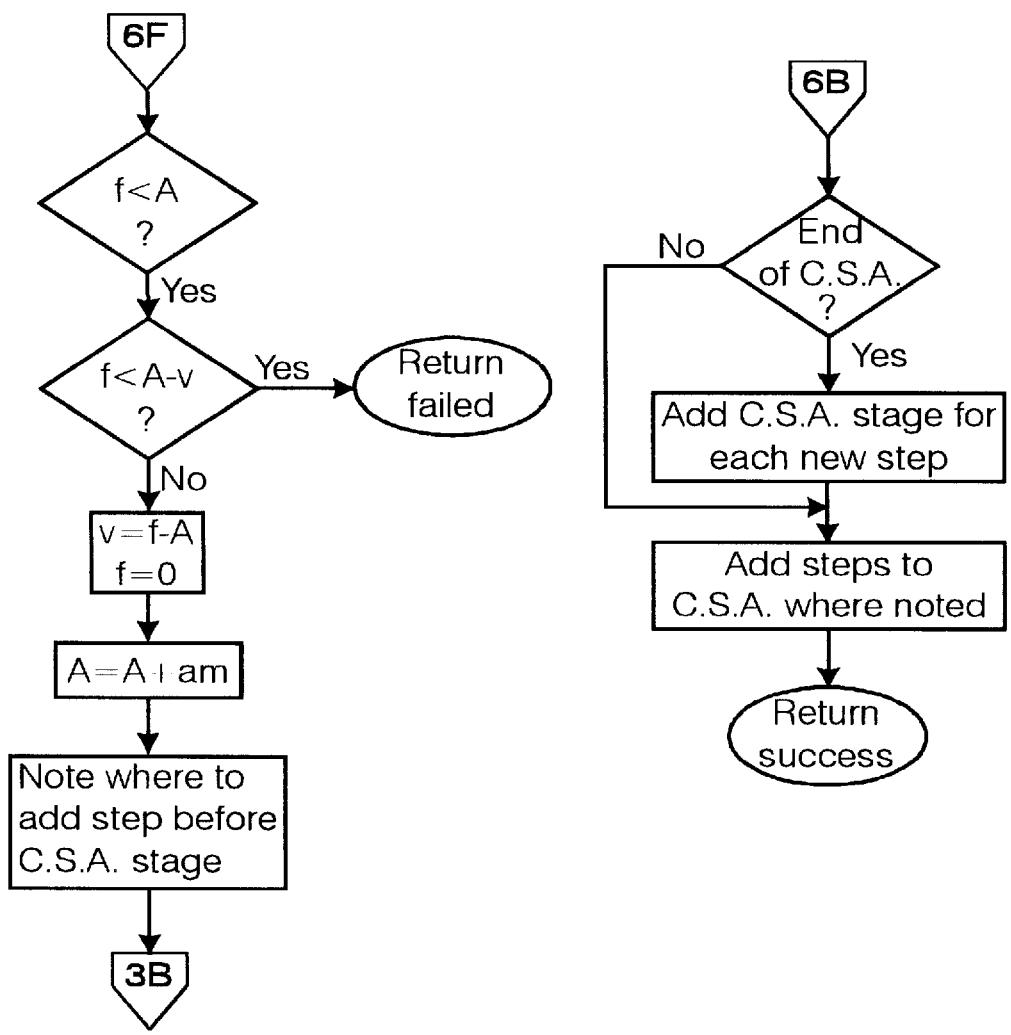

FIG. 21 illustrates a summary of how the autostainer control program calculates the most efficient dispensing pattern. Referring to FIG. 21, at step 2105 the control program first groups together the slides in each step that have the same reagents and same incubation times. The same protocol scheduling number is assign to groups with the same incubation time. An array is created for each group that contains an action time (the amount of time required to pick up and dispense reagent), a fixed time (the incubation time that follow the action time), and a variable time (10% of the fixed time) for each protocol step.

At step 2110, a first group is selected as the "Currently Scheduled Array (CSA)." The control program then adds additional groups to the Currently Scheduled Array. At step 2115 an unscheduled group is selected. Next, at step 2120, the selected group is fitted into the Currently Scheduled Array by adding to the action times within the fixed and variable times. FIGS. 22a through 22d illustrate in detail how a group is added to a currently scheduled Array.

Step 2125 tests if the group fit into the Currently Scheduled Array. If it did not fit, then the control program proceeds to step 2130 where it tests to see if it has tried 10 times to make it fit. If it has not tried 10 times yet, then in will try again. Since the variable time is randomized each try it may fit on another attempt. If it has tried 10 times, the control program proceeds to step 2135 where it sees if it has tried to fit all the groups in the Currently Scheduled Array. If it has not tried to fit all the groups in yet, then it moves to step 2140 where another group is selected and then back to step 2120 where it tries to fit that group in. If all groups have been tried, then the control program moves to step 2150 where it moves to the next stage in the Currently Scheduled Array and then back to step 2120 where it tries to fit that group in.

Referring back to step 2125 when a group fits into the schedule, the control program then tests if all the groups have been scheduled. If all the groups have not been scheduled then the control program proceeds back to step 2115 to schedule another unscheduled group. If all the groups have been scheduled, then the control program then tests if it has tried 100 different times to schedule the program. If it has not tried 100 times, then the control program moves to step 2110 to program another schedule. Again, since the variable times are randomized, each try schedule will be different.

Figure 23:
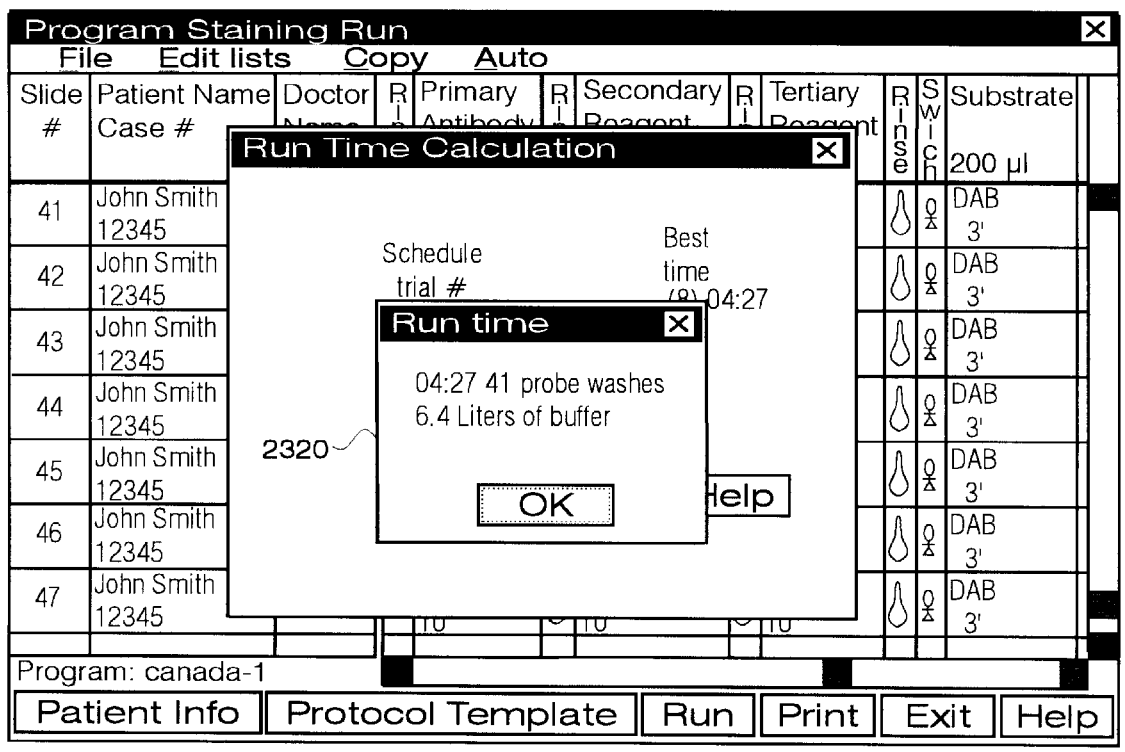
FIG. 23 illustrates the Run Time Calculation Window and the Run Time Dialogue Window of the autostainer control program.

While the autostainer control program calculates, the control program displays the number of tries and the best time in a Run Time Calculation Screen as illustrated in FIG. 23. When the autostainer control program is finished calculating the most efficient dispensing pattern, then a Run Time dialogue window 2320 displayed. The Run Time dialogue window 2320 lists how long the staining run will take, how many times the probe will be washed, and how much buffer solution will be required for the staining run. The user clicks "OK" to proceed to the Reagent Layout Map Screen.

FIG. 24 illustrates the Reagent Layout Map Screen of the autostainer control program. The Reagent Layout Map Screen graphically displays a map of how the reagents should be loaded into the 32 vial reagent rack. Each vial is displayed with an alphanumeric rack position, the abbreviated reagent name, and the amount of reagent that is required.

Figure 25:
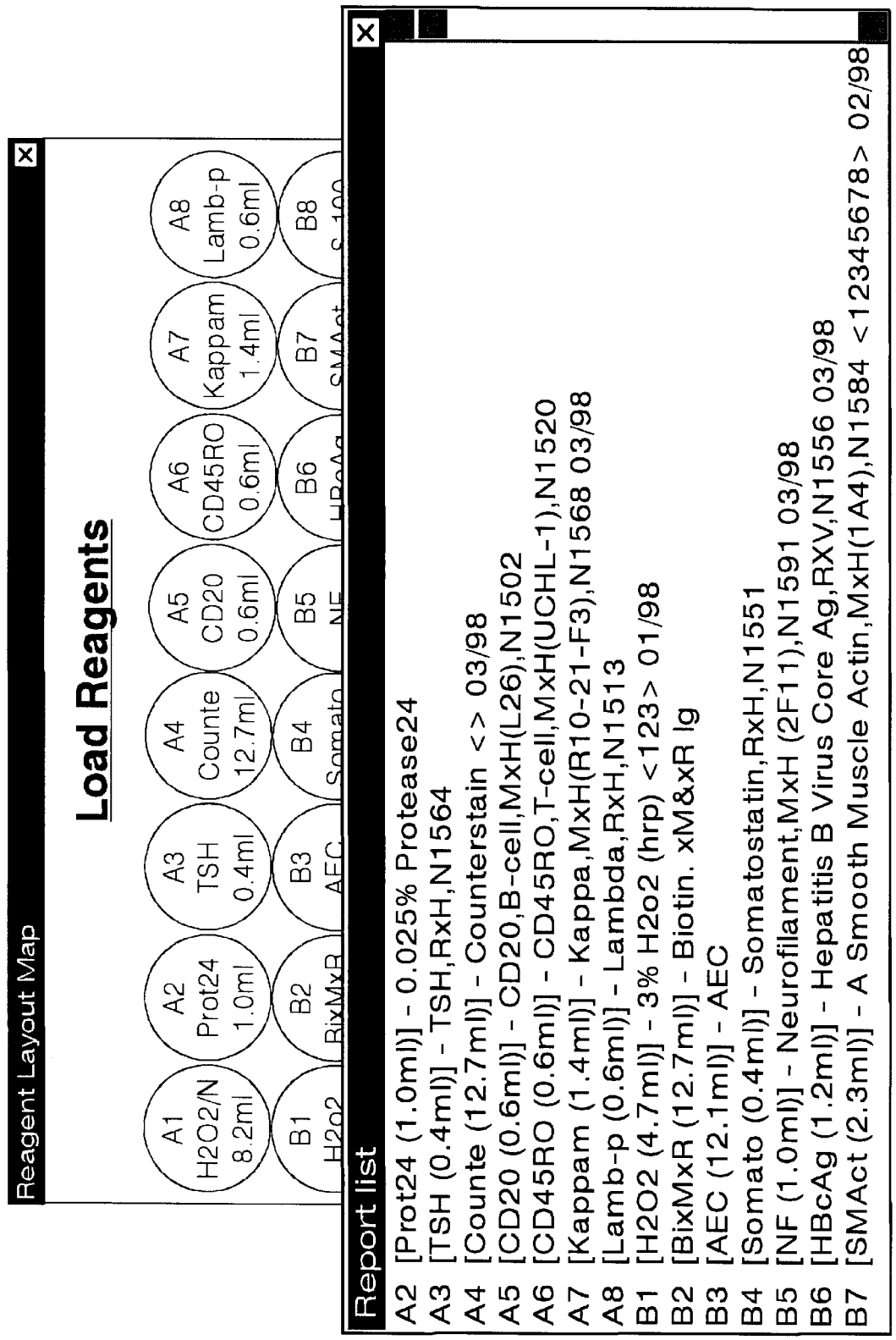
FIG. 25 illustrates the Reagent Layout Map Screen of the autostainer control program with a reagent list window displayed.

The Reagent Layout Map Screen includes several function buttons. When the user selects the Reagent List button 2410, the Reagent list appears as depicted in FIG. 25 and displays a detailed listing of the reagents used in the current staining run. Referring back to FIG. 24, the Prime Pump button 2430 primes the pump by allowing buffer solution to flow out of the wash head. The Cancel button 2470 cancels the current staining run and returns to the Program Staining Run Screen. The Slide Map button 2420 returns to the previous Slide Layout Map Screen. The Print button 2460 prints out the reagent layout map. The Second Rack button 2440 displays a second rack of the reagents. (The Second Rack button 2440 only appears if there are so many reagents required in the current staining run that a second reagent rack is required.) The OK button 2450 starts the current staining run. The user selects the OK button 2450 only after all the required reagents have been loaded into the reagent rack.

Figure 26:
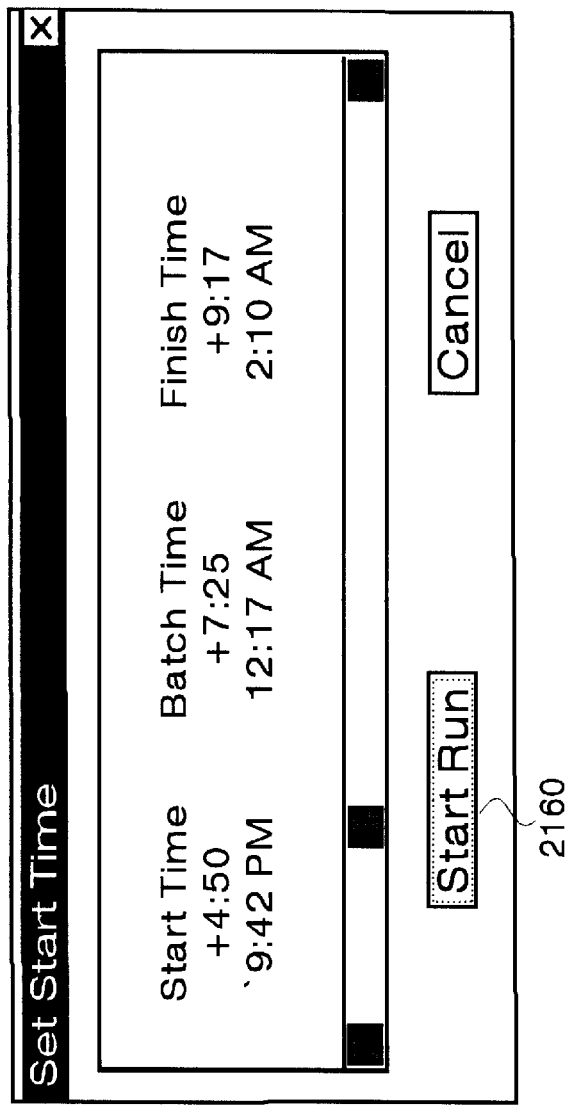
FIG. 26 illustrates the Set Start Time Window of the autostainer control program.
Figure 27:
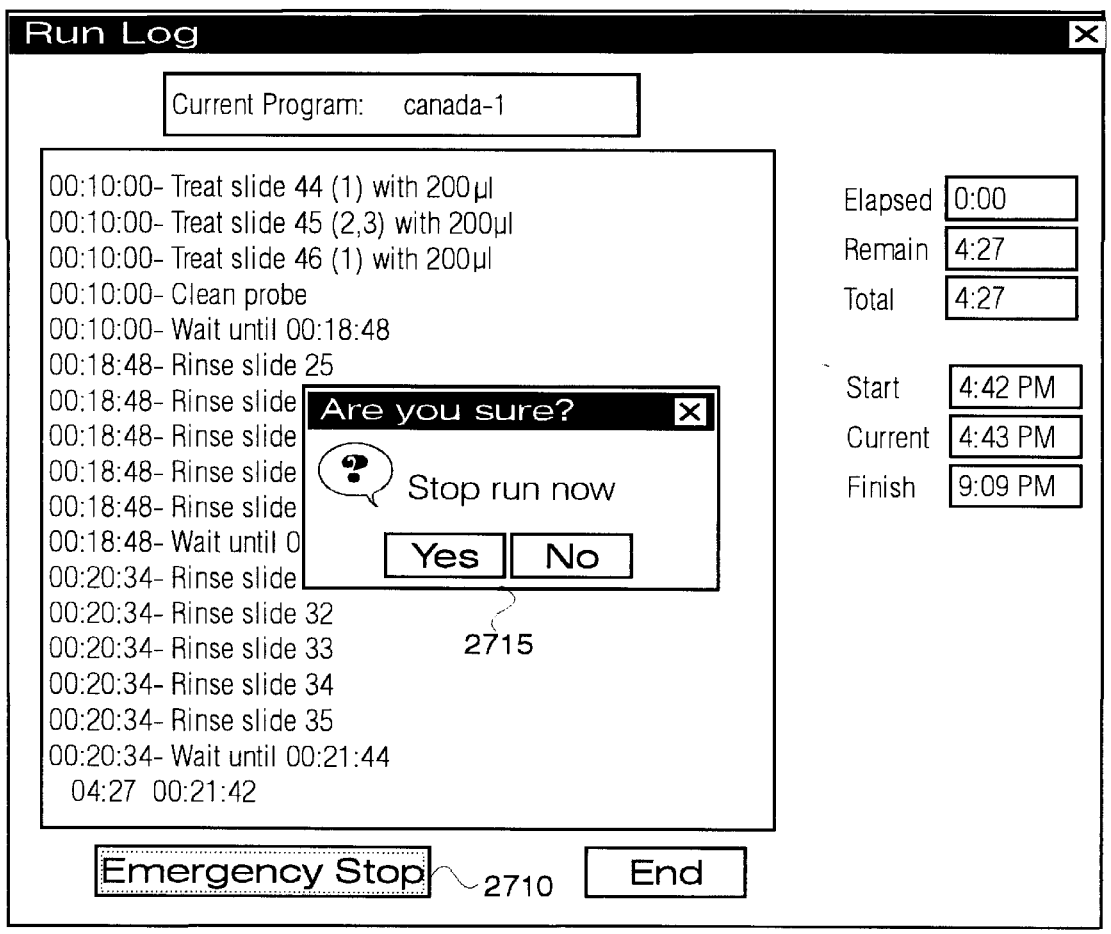
FIG. 27 illustrates the Run Log Screen of the autostainer control program.

After selecting the OK button on the Reagent Layout Map Screen, the autostainer displays a Set Start Time Window as illustrated in FIG. 26. The Set Start Time Window allows the user to select when the autostainer will begin the staining run. If the user selects a large delay, the autostainer control program will request additional buffer solution to keep the slides moist. When the user selects the Start button 2610, the autostainer control program begins the staining run. At this point the Run Log Screen of FIG. 27 is displayed on the control computer's screen. The Run Log Screen displays detailed information log of the steps being performed along with a time stamp for each step. The Run Log Screen displays the start time, the current time, and the projected finish time. To keep track of the current staining run, the Run Log Screen displays the elapsed time, the projected remaining time, and the projected total run time.

The current staining run can be paused by selecting the "Emergency Stop" button 2710 the Run Log Screen. This will cause an "Are you sure" dialogue window 2715 to be displayed. The dialogue window 2715 allows the current staining run to be resumed or aborted.

During the staining run, each slide is processed exactly as the protocol has been programmed for that slide. To avoid contamination, the autostainer head moves in between the reagent vials and glass slides after reagent has been picked up.

As stated earlier, the reagent probe includes custom circuitry that allows the probe to sense liquid levels. During a staining operation, this feature is used to determine if there is enough reagent. When there is not enough reagent to complete a staining run, the autostainer control program stops and a dialogue window appears which informs the user about the problem. If the user responds to the dialogue window, then the autostainer control program will move the Z head assembly out of the way and will display a Reagent Layout Map Screen showing the type, amount, and location of the reagent to be added. This allows the user to correct the problem. If the user does not respond within a minute, then the autostainer control program will use what reagent is available and continue operation. The autostainer control program will soon again stop and warn the user of the insufficient reagent. Again, if there is no response from the user, the autostainer control program will continue the staining run without the needed reagent. When there is insufficient reagent to satisfy the immediate need, the autostainer control program will skip the slides that need the missing reagent and note that in the run log.

While the autostainer control program is performing the staining run, the personal computer can be used to run other programs as long as the autostainer control program is being executed on a multitasking operating system such as Windows® 95 from Microsoft® Corporation of Redmond, Wash. In the present embodiment, a separate programs are used to program a staining run and to run a staining run. Thus, while the staining run execution program is running, a user can execute the staining run programming program in order to program future staining runs.

After the staining run has completed, an "End Program Run" dialog box will be displayed and the computer will beep occasionally. At this point the user can print out a full copy of the program run log such that an Immunohistochemical Report can be created. The run information for any particular slide can be later recalled and used in conjunction with images of the stained slide captured with a CCD camera. Thus, a complete history of each slide will be available for analysis and diagnosis.

The foregoing has described a method and apparatus for automatic tissue and cell preparation staining. It is contemplated that changes and modifications may be made by one of ordinary skill in the art, to the materials and arrangements of elements of the present invention without departing from the scope of the invention.

We claim:

1. A computer implemented method of programming an autostainer device, said method comprising the steps of:

accepting input from a user to select a first reagent for a first slide;

accepting input from a user to select a second reagent for said first slide;

comparing said first reagent with said second reagent for compatibility; and warning said user if said first reagent is incompatible with said second reagent.

2. The method as claimed in claim 1 wherein said step of comparing said first reagent with said second reagent for compatibility comprises testing for species reactivity compatibility.

3. The method as claimed in claim 1 wherein said step of comparing said first reagent with said second reagent for compatibility comprises testing for enzyme system compatibility.

4. An apparatus for holding slides in an automated slide preparation device, said apparatus comprising:

at least one slide position, each said slide position comprising a slide clip for grasping only a frosted end of a glass slide.

5. The apparatus for holding slides as claimed in claim 4 wherein each said slide position has drainage openings proximate to said slide clip, said drainage openings allow excess buffer solution to drain away.

6. The apparatus for holding slides as claimed in claim 4 wherein said said slide clip contacts a top side of said frosted end of said glass slide.

7. The apparatus for holding slides as claimed in claim 4 wherein said slide clip holds said glass slide in a horizontal position.

8. An apparatus for preparing slides, said apparatus comprising:

an automatic staining apparatus, said automatic staining apparatus having capacity for a plurality of slides, said automatic staining apparatus for dispensing reagents onto said slides, said plurality of slides comprising a first set of slides and a second set of slides, said automatic staining apparatus responsive to a set of electrical commands;

a computer system, said computer system coupled to said automatic staining apparatus for delivering said set of electrical commands; and an autostainer control program, said autostainer control program executing a first set of programmable protocol steps for said first set of said slides and said autostainer control program executing a second set of programmable protocol steps for said second set of said slides.

9. The apparatus for preparing slides as claimed in claim 8 further comprising:

an autostainer protocol editor program, said autostainer protocol editor program for programming said first and said second set of programmable protocol steps for said first and said second set of said slides, respectively.

10. An apparatus for preparing slides, said apparatus comprising:

a plurality of slides;

a delivery system for dispensing reagents on said slides;

a reservoir for collecting reagents washed off said slides;

a first pump for removing nonhazardous waste from said reservoir; and a second pump for removing hazardous waste from said reservoir.

11. The apparatus for preparing slides as claimed in claim 10 further comprising:

a rinse solution delivery system, said rinse solution delivery system for washing reagents off said slides.

12. The apparatus for preparing slides as claimed in claim 10 further comprising:

an autostainer control program for determining when to switch between nonhazardous waste collection in said reservoir and hazardous waste collection in said reservoir.

13. An apparatus for preparing slides, said apparatus comprising:

a reagent rack for storing a plurality of different reagents;

a slide rack for holding a plurality of slides;

a robotic motion control system, said robotic motion control system having a probe for dispensing reagent from said reagent rack onto said slides; and a washbin, said robotic motion control system washes said probe in said washbin between the use of different reagents in said reagent rack.

14. The apparatus for preparing slides as claimed in claim 13 further comprising:

an autostainer control program, said autostainer control program for determining an amount of rinse solution that will be required during a staining run, said amount of rinse solution required displayed to a user.

15. The apparatus as claimed in claim 13 wherein said probe is Teflon coated.

16. The apparatus as claimed in claim 13 wherein said washbin comprises a first receptacle for washing an inside of said probe and a second receptacle for washing an outside of said probe.

17. A computer implemented method of programming an autostaining apparatus, said method comprising the steps of:

graphically displaying a first list of possible protocol steps on a computer display;

graphically displaying a second list of selected protocol steps; and accepting input from a user to move protocol steps from said list of possible protocol steps to said list of selected protocol steps; and saving said second list of selected protocol steps for future use.

18. The computer implemented method of programming an autostaining apparatus as claimed in claim 17 wherein said method further comprises the steps of:

accepting input from said user to assign reagents to regent protocol steps in said list of selected protocol steps.

19. The computer implemented method of programming an autostaining apparatus as claimed in claim 17 wherein said method further comprises the steps of:

periodically displaying a maintenance message informing said user that routine maintenance should be performed on said autostaining apparatus.

20. A computer implemented method of programming an slide preparation apparatus, said method comprising the steps of:

displaying a grid comprising a plurality of tiles on a computer display, a first axis of said grid corresponding to a set of slides to be prepared and a second axis of said grid corresponding to a set of protocol steps to be performed on said slides;

accepting input from a user to select particular tile; and displaying edit information about said particular tile in response to said input from said user.

21. The computer implemented method of programming an slide preparation apparatus as claimed in claim 20 wherein said selected tile represents a step of dispensing a reagent type and said step of displaying edit information comprises displaying an edit window with information about said reagent.

22. The computer implemented method of programming an slide preparation apparatus as claimed in claim 21 wherein said edit window allows the selection of a particular reagent.

23. The computer implemented method of programming an slide preparation apparatus as claimed in claim 21 further comprising the steps of:

accepting input from said user about said reagent; and displaying a request to said user ask if the input from said user about said reagent should be applied to the remaining unprogrammed slides.

24. The computer implemented method of programming an slide preparation apparatus as claimed in claim 20 wherein said selected tile represents a step of dispensing a reagent type and said step of displaying edit information comprises displaying a list of possible reagents.

25. The computer implemented method of programming an slide preparation apparatus as claimed in claim 20 further comprising the steps of:

accepting input from said user to select a set of tiles and copy said tiles; and accepting input from said user to paste said set of copied tiles.

26. The computer implemented method of programming an slide preparation apparatus as claimed in claim 20 wherein each row of protocol steps along said second axis representing steps to be performed on a slide can be different from each other row.

27. An air nozzle for aspiration slides in a slide processing apparatus, said air nozzle comprising:

an air supply line for supplying pressurized air; and a head assembly, said head assembly having an internal well for equalizing the air pressure, said head assembly having a narrow slit that allows air to escape in a two dimensional fan spray pattern.

28. The air nozzle for aspirating slides as claimed in claim 27 wherein said head assembly includes an internal well for equalizing the air pressure before the air exits through said narrow slit.

29. The air nozzle for aspirating slides as claimed in claim 27 wherein said air exits through the narrow slit onto slides at approximately a forty-five degree angle.

* * * * *